(12) United States Patent
Pierard et al.

(10) Patent No.: US 8,461,149 B2
(45) Date of Patent: Jun. 11, 2013

(54) COMPOUNDS USEFUL AS PROTEIN KINASE INHIBITORS

(75) Inventors: Francoise Pierard, Abingdon (GB); Jean-Damien Charrier, Abingdon (GB)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 193 days.

(21) Appl. No.: 12/673,287

(22) PCT Filed: Aug. 15, 2008

(86) PCT No.: PCT/US2008/009786
§ 371 (c)(1),
(2), (4) Date: May 25, 2011

(87) PCT Pub. No.: WO2009/023269
PCT Pub. Date: Feb. 19, 2009

(65) Prior Publication Data
US 2011/0263575 A1    Oct. 27, 2011

Related U.S. Application Data

(60) Provisional application No. 60/980,629, filed on Oct. 17, 2007, provisional application No. 60/964,825, filed on Aug. 15, 2007.

(51) Int. Cl.
*C07D 487/04* (2006.01)
*A61K 31/551* (2006.01)

(52) U.S. Cl.
USPC ........ 514/220; 514/221; 514/250; 514/262.1; 540/495; 540/502; 544/252; 544/258

(58) Field of Classification Search
USPC ........... 540/495, 502; 544/252, 258; 514/220, 514/221, 250, 262.1
See application file for complete search history.

(56) References Cited

U.S. PATENT DOCUMENTS

2006/0004014 A1    1/2006    Hoffman et al.

FOREIGN PATENT DOCUMENTS

| WO | 2006/041773 A2 | 4/2006 |
|----|----------------|--------|
| WO | 2007/095188 A2 | 8/2007 |
| WO | 2008/003958 A2 | 1/2008 |
| WO | 2008/113711 A1 | 9/2008 |
| WO | 2009/040556    | 4/2009 |
| WO | 2010/008454    | 1/2010 |
| WO | 2010/008459    | 1/2010 |

OTHER PUBLICATIONS

WO 2009/023269 International Search Report, (2009).
PCT/US2008/009786 Written Opinion, (2008).
International Search Report issued for PCT/US2009/003716 Dated Nov. 20, 2009.
International Search Report issued for PCT/US2009/003723 Dated Nov. 20, 2009.

*Primary Examiner* — Bruck Kifle
(74) *Attorney, Agent, or Firm* — Honigman Miller Schwartz and Cohn LLP; Andrew N. Weber; Jonathan P. O'Brien

(57) ABSTRACT

The present invention relates to compounds useful as inhibitors of protein kinase. The invention also provides pharmaceutically acceptable compositions comprising said compounds and methods of using the compositions in the treatment of various disease, conditions, or disorders.

34 Claims, No Drawings

SEQUENCE LISTING

```
<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 1

Lys Lys Lys Ile Ser Asp Glu Leu Met Asp Ala Thr Phe Ala Asp Gln
1               5                   10                  15

Glu Ala Lys

<210> SEQ ID NO 2
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 2

Lys Lys Lys Met Asp Ala Thr Phe Ala Asp Gln
1               5                   10
```

COMPOUNDS USEFUL AS PROTEIN KINASE INHIBITORS

CROSS REFERENCE TO RELATED APPLICATION

This U.S. utility application claims priority from PCT/US2008/009786, filed Aug. 15, 2008, which claims priority from U.S. provisional application No. 60/964,825 filed on Aug. 15, 2007 and U.S. provisional application No. 60/980,629 filed Oct. 17, 2007. Each of the aforementioned applications is incorporated herein by reference in their entireties.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders. The invention also provides processes for preparing the compounds of the invention.

BACKGROUND OF THE INVENTION

The search for new therapeutic agents has been greatly aided in recent years by a better understanding of the structure of enzymes and other biomolecules associated with diseases. One important class of enzymes that has been the subject of intensive study is protein kinases.

Protein kinases constitute a large family of structurally related enzymes that are responsible for the control of a variety of signal transduction processes within the cell (see Hardie, G and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids etc). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al, *Cell* 1992, 70, 419-429; Kunz et al, *Cell* 1993, 73, 585-596; Garcia-Bustos et al, *EMBO J* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., shock, heat shock, ultraviolet radiation, bacterial endotoxin, and $H_2O_2$), cytokines (e.g., interleukin-1 (IL-1) and tumor necrosis factor alpha (TNF-a), and growth factors (e.g., granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Many diseases are associated with abnormal cellular responses triggered by protein kinase-mediated events as described above. These diseases include, but are not limited to, cancer, autoimmune diseases, inflammatory diseases, bone diseases, metabolic diseases, neurological and neurodegenerative diseases, cardiovascular diseases, allergies and asthma, Alzheimer's disease and hormone related diseases. Accordingly, there has been a substantial effort in medicinal chemistry to find protein kinase inhibitors that are effective as therapeutic agents.

The Polo-like kinases (PLK) belong to a family of serine/threonine kinases that are highly conserved across the species, ranging from yeast to man (reviewed in Lowery D M et al., *Oncogene* 2005, 24; 248-259). The PLK kinases have multiple roles in cell cycle, including control of entry into and progression through mitosis.

PLK1 is the best characterized of the PLK family members. PLK1 is widely expressed and is most abundant in tissues with a high mitotic index. Protein levels of PLK1 rise and peak in mitosis (Hamanaka, R et al., *J Biol Chem* 1995, 270, 21086-21091). The reported substrates of PLK1 are all molecules that are known to regulate entry and progression through mitosis, and include CDC25C, cyclin B, p53, APC, BRCA2 and the proteasome. PLK1 is upregulated in multiple cancer types and the expression levels correlate with severity of disease (Macmillan, J C et al., *Ann Surg Oncol* 2001, 8, 729-740). PLK1 is an oncogene and can transform NIH-3T3 cells (Smith, M R et al., *Biochem Biophys Res Commun* 1997, 234, 397-405). Depletion or inhibition of PLK1 by siRNA, antisense, microinjection of antibodies, or transfection of a dominant negative construct of PLK1 into cells, reduces proliferation and viability of tumour cells in vitro (Guan, R et al., *Cancer Res* 2005, 65, 2698-2704; Liu, X et al., Proc Natl Acad Sci USA 2003, 100, 5789-5794, Fan, Y et al., *World J Gastroenterol* 2005, 11, 4596-4599; Lane, H A et al., *J Cell Biol* 1996, 135, 1701-1713). Tumour cells that have been depleted of PLK1 have activated spindle checkpoints and defects in spindle formation, chromosome alignment and separation and cytokinesis. Loss in viability has been reported to be the result of an induction of apoptosis. In contrast, normal cells have been reported to maintain viability on depletion of PLK1. In vivo knock down of PLK1 by siRNA or the use of dominant negative constructs leads to growth inhibition or regression of tumours in xenograft models.

PLK2 is mainly expressed during the G1 phase of the cell cycle and is localized to the centrosome in interphase cells. PLK2 knockout mice develop normally, are fertile and have normal survival rates, but are around 20% smaller than wild type mice. Cells from knockout animals progress through the cell cycle more slowly than in normal mice (Ma, S et al., *Mol Cell Biol* 2003, 23, 6936-6943). Depletion of PLK2 by siRNA or transfection of kinase inactive mutants into cells blocks centriole duplication. Downregulation of PLK2 also sensitizes tumour cells to taxol and promotes mitotic catastrophe, in part by suppression of the p53 response (Burns T F et al., *Mol Cell Biol* 2003, 23, 5556-5571).

PLK3 is expressed throughout the cell cycle and increases from G1 to mitosis. Expression is upregulated in highly proliferating ovarian tumours and breast cancer and is associated with a worse prognosis (Weichert, W et al., *Br J Cancer* 2004, 90, 815-821; Weichert, W et al., *Virchows Arch* 2005, 446, 442-450). In addition to regulation of mitosis, PLK3 is believed to be involved in Golgi fragmentation during the cell cycle and in the DNA-damage response. Inhibition of PLK3 by dominant negative expression is reported to promote p53- independent apoptosis after DNA damage and suppresses colony formation by tumour cells (Li, Z et al., *J Biol Chem* 2005, 280, 16843-16850).

PLK4 is structurally more diverse from the other PLK family members. Depletion of this kinase causes apoptosis in cancer cells (Li, J et al., *Neoplasia* 2005, 7, 312-323). PLK4 knockout mice arrest at E7.5 with a high fraction of cells in mitosis and partly segregated chromosomes (Hudson, J W et al., *Current Biology* 2001, 11, 441-446).

Molecules of the protein kinase family have been implicated in tumour cell growth, proliferation and survival. Accordingly, there is a great need to develop compounds useful as inhibitors of protein kinases. The evidence implicating the PLK kinases as essential for cell division is strong. Blockade of the cell cycle is a clinically validated approach to inhibiting tumour cell proliferation and viability. It would therefore be desirable to develop compounds that are useful as inhibitors of the PLK family of protein kinases (e.g., PLK1, PLK2, PLK3 and PLK4), that would inhibit proliferation and reduce viability of tumour cells, particularly as there is a strong medical need to develop new treatments for cancer, including treatments that would be administered orally.

SUMMARY OF THE INVENTION

Compounds of this invention, and pharmaceutically acceptable compositions thereof, are useful as inhibitors of protein kinases. In some embodiments, these compounds are useful as inhibitors of PLK protein kinases; in some embodiments, as inhibitors of PLK1 protein kinases. These compounds have the formula I, as defined herein or pharmaceutically acceptable salts thereof.

These compounds, and pharmaceutically acceptable salts thereof, are useful for treating or preventing a variety of diseases, disorders or conditions, including, but not limited to, an autoimmune, inflammatory, proliferative, or hyperproliferative disease, a neurodegenerative disease, or an immunologically-mediated disease. The compounds provided by this invention are also useful for the study of kinases in biological and pathological phenomena; the study of intracellular signal transduction pathways mediated by such kinases; and the comparative evaluation of new kinase inhibitors.

In some instances, the compounds of this invention demonstrate PLK1 inhibition at concentrations of less than 1 nM. In other instances, the compounds of this invention demonstrate PLK1 inhibition at concentrations of between 1 nM and 10 nM. Further, the compounds of the invention demonstrate advantageous phrmaco-kinetic properties.

DETAILED DESCRIPTION OF THE INVENTION

In one aspect, the invention features a compound of formula I:

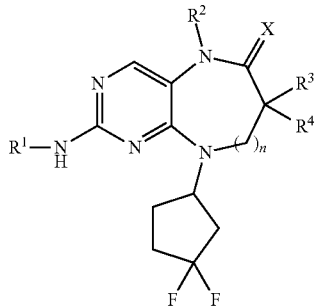

wherein:

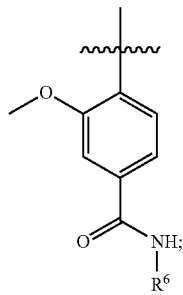

$R^1$ is $R^6$ is $C_{1-4}$ aliphatic or $C_{3-6}$ cycloaliphatic, and is substituted with 1 to 2 halogen atoms (e.g., fluorine);

X is O and $R^2$ is $CH_3$; or X is $NR^5$ and, $R^2$ and $R^5$, together with the atoms to which they are attached, form a 1,2,4-triazole;

each of $R^3$ and $R^4$ is independently H, methyl, or ethyl; or $R^3$ and $R^4$, together with the atoms to which they are attached, form a cyclopropyl ring; and n is 0 or 1.

Embodiments of the compound of this invention may include one or more of the following features: X is O and $R^2$ is —$CH_3$; $R^6$ is a $C_{3-6}$ cycloaliphatic optionally substituted with 1 to 2 halogen (e.g., fluorine) atoms; $R^3$ is methyl; $R^4$ is methyl; $R^3$ is H; $R^4$ is ethyl; $R^6$ is cyclopropyl optionally substituted with 1 to 2 fluorine atoms; $R^6$ is cyclopentyl optionally substituted with 1 to 2 halogen (e.g., fluorine) atoms; $R^6$ is cyclohexyl optionally substituted with 1 to 2 halogen (e.g., fluorine) atoms; $R^6$ is $C_{1-4}$ aliphatic optionally substituted with 1 to 2 halogen (e.g., fluorine) atoms.

Specific examples of the compounds of this invention include, but are mot limited to, N-cyclopropyl-4-(9-(3,3-difluorocyclopentyl)-5,7,7-trimethyl-6-oxo-6,7,8,9-tetrahydro-5H-pyrimido[4,5-b][1,4]diazepin-2-ylamino)-3-methoxybenzamide;

4-(9-(3,3-difluorocyclopentyl)-5,7,7-trimethyl-6-oxo-6,7,8,9-tetrahydro-5H-pyrimido[4,5-b][1,4]diazepin-2-ylamino)-N-(3-fluorocyclopentyl)-3-methoxybenzamide;

N-(3,3-difluorocyclopentyl)-4-(9-(3,3-difluorocyclopentyl)-5,7,7-trimethyl-6-oxo-6,7,8,9-tetrahydro-5H-pyrimido[4,5-b][1,4]diazepin-2-ylamino)-3-methoxybenzamide;

N-cyclopropyl-4-(9'-(3,3-difluorocyclopentyl)-5'-methyl-6'-oxo-5',6',8',9'-tetrahydrospiro[cyclopropane-1,7'-pyrimido[4,5-b][1,4]diazepine]-2'-ylamino)-3-methoxybenzamide;

N-(3,3-difluorocyclopentyl)-4-(9'-(3,3-difluorocyclopentyl)-5'-methyl-6'-oxo-5',6',8',9'-tetrahydrospiro[cyclopropane-1,7'-pyrimido[4,5-b][1,4]diazepine]-2'-ylamino)-3-methoxybenzamide;

4-((R)-5-((R)-3,3-difluorocyclopentyl)-4-ethyl-4,5-dihydro-[1,2,4]triazolo[4,3-f]pteridin-7-ylamino)-N-ethyl-3-methoxybenzamide;

N-cyclopropyl-4-((R)-5-((R)-3,3-difluorocyclopentyl)-4-ethyl-4,5-dihydro-[1,2,4]triazolo[4,3-f]pteridin-7-ylamino)-3-methoxybenzamide;

4-((R)-8-((R)-3,3-difluorocyclopentyl)-7-ethyl-5-methyl-6-oxo-5,6,7,8-tetrahydropteridin-2-ylamino)-N-ethyl-3-methoxybenzamide; and N-cyclopropyl-4-((R)-8-((R)-3,3-difluorocyclopentyl)-7-ethyl-5-methyl-6-oxo-5,6,7,8-tetrahydropteridin-2-ylamino)-3-methoxybenzamide.

In some embodiments, the compounds of formula I are of formula I-A:

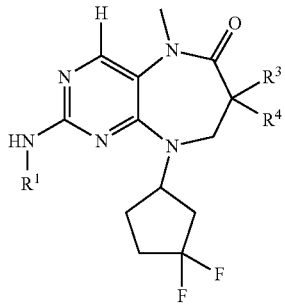
I-A

In some other embodiments, the compounds of formula I are of formula I-B:

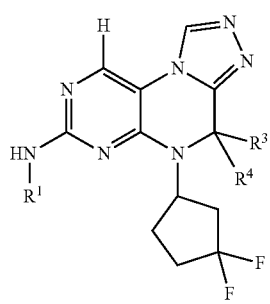
I-B

In still some other embodiments, the compounds of formula I are of formula I-C:

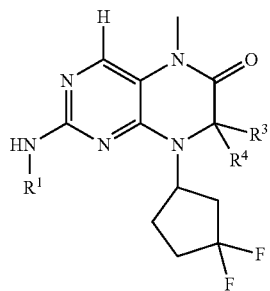
I-C

In some embodiments when the compounds of formula I are of formula I-A, $R^3$ and $R^4$ are each methyl; or, one of $R^3$ and $R^4$ is H and the other one is methyl; or, $R^3$ and $R^4$, together with the atoms to which they are attached, form cyclopropyl.

In some other embodiments when the compounds of formula I are of formula I-B, one of $R^3$ and $R^4$ is H and the other one is ethyl; and the asymmetric carbon has an (R) configuration as shown below.

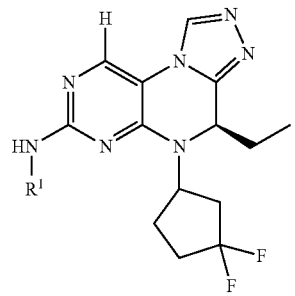
I-B(R)

In some other embodiments when the compounds of formula are of formula I-C, one of $R^3$ and $R^4$ is H and the other one is ethyl; and the asymmetric carbon has an (R) configuration as shown below.

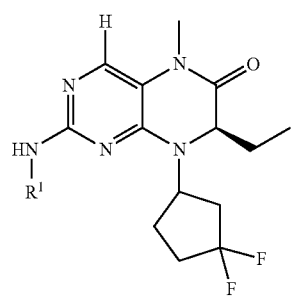
I-C(R)

In some embodiments of the compounds of this invention, $R^1$ is

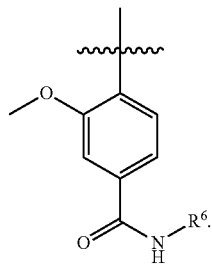

In another aspect, the present invention provides a process for preparing a compound of formula I-A:

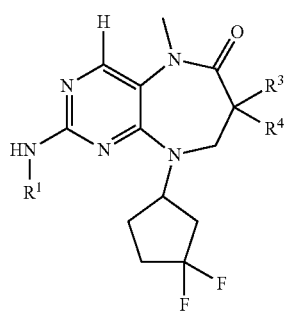
I-A

In formula I-A, $R^1$ is

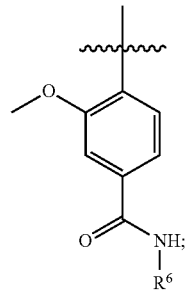

$R^6$ is $C_{1-4}$ aliphatic or $C_{3-6}$ cycloaliphatic, and is optionally substituted with 1 or 2 halogen atoms (e.g., 2 fluorine atoms); and each of $R^3$ and $R^4$ is independently H, methyl, or ethyl; or $R_3$ and $R_4$, together with the atoms to which they are attached, form a cyclopropyl ring. This process includes the step of reacting a compound of formula 5A:

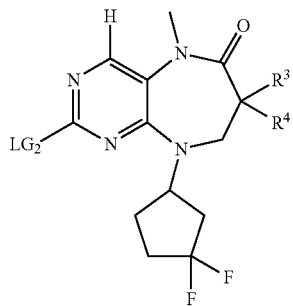

5A wherein $LG_2$ is a leaving group, with $H_2NR^1$ to form the compound of formula I-A.

In some embodiments, the process further includes the step of reacting a compound of formula 4A:

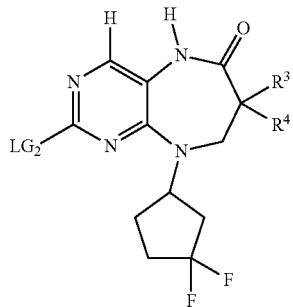

4A with Me-$LG_3$, wherein $LG_3$ is a leaving group capable of being displaced by an NH amide under suitable conditions, to form the compound of formula 5A.

In some other embodiments, the process further includes the step of reductive cyclization of a compound of formula 3A:

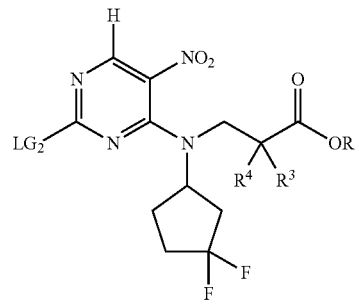

3A wherein R is $C_{1-6}$ aliphatic or hydrogen, to form a compound of formula 4A.

In still some other embodiments, the process further includes cyclizing a compound of formula 3A-a:

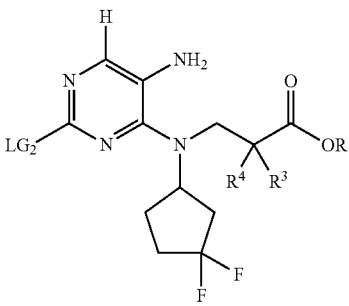

3A-a under cyclo-condensation conditions to form a compound of formula 4A.

In yet still some other embodiments, the process further includes the step of reacting a compound of formula 3A:

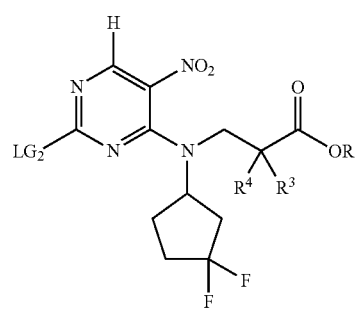

3A under reduction conditions to form a compound of formula 3A-a.

Examples of suitable reduction conditions are described in, e.g., J. W. Bae et al., *Chem. Commun.*, 2000, 1857-1858 (N-alkylaminobenzenes were prepared in a simple and efficient one-pot synthesis by reduction of nitrobenzenes followed by reductive amination with decaborane (B10H14) in the presence of 10% Pd/C); R. J. Rahaim et al., *Org. Lett.*, 2005, 7, 5087-5090 (palladium-catalyzed reduction of aromatic nitro groups to amines can be accomplished in high yield, with wide functional group tolerance and short reaction times at r.t. using aqueous potassium fluoride and polymethylhydrosiloxane (PMHS) for aromatic nitro groups; Aliphatic nitro compounds are reduced to the corresponding hydroxylamines using triethylsilane instead of PMHS/KF); G. S. Vanier, Synlett, 2007, 131-135 (a generally applicable method for the introduction of gaseous hydrogen into a sealed reaction system under microwave irradiation allows the hydrogenation of various substrates in short reaction times with moderate temperatures between 80° C. and 100° C. with 50 psi of hydrogen); S. Chandrasekhar et al., *J. Org. Chem.*, 2006, 71, 2196-2199 (poly(ethylene glycol) (PEG) (400) has been found to be a superior solvent over ionic liquids by severalfold in promoting the hydrogenation of various functional groups using Adams' catalyst; both the catalyst and PEG were recycled efficiently over 10 runs without loss of activity, and without substrate cross contamination); H. Berthold et al., *Synthesis*, 2002, 1607-1610 (a microwave-assisted, palladium-catalyzed catalytic transfer hydrogenation of different homo- or heteronuclear organic compounds using formate salts as a hydrogen source was performed in ([bmim][PF6]; essentially pure products could be isolated in moderate to excellent yields by simple liquid-liquid extraction); and C. Yu et al., *J. Org. Chem.*, 2001, 66, 919-924 (a mild and efficient electron-transfer method for the chemoselective reduction of aromatic nitro groups using samarium(0) metal in the presence of a catalytic amount of 1,1'-dioctyl-4,4'-bipyridinium dibromide gives aromatic amines in good yield with selectivity over a number of other functional and protecting groups).

In yet still some other embodiments, the process further includes the steps of (a) reacting the compound of formula 3A-a with an alkylating agent under suitable conditions to form a compound of formula 3A-b;

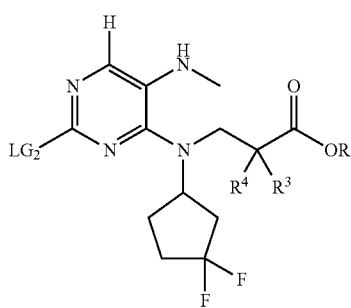

3A-b and (b) cyclizing the compound of formula 3A-b under suitable cyclo-condensation conditions to form a compound of formula 5A. Examples of alkylating agents include alkyl halide. See, e.g., U.S. Pat. No. 4,783,554.

In still some other embodiments, the process further includes reacting a compound of formula 2a:

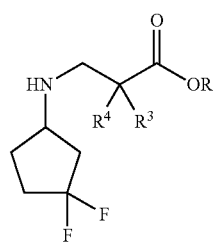

2a with a compound of formula 1:

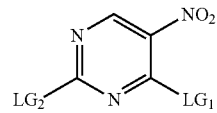

1 under suitable displacement conditions to form the compound of formula 3A.

In some other embodiments, the process further includes reacting a compound of formula 11:

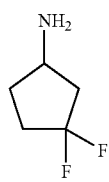

11 with a compound of formula 12:

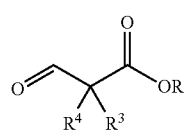

12 under suitable reductive amination conditions to form the compound of formula 2a.

In yet still other embodiments, the process further includes the steps of (a) reacting compound of formula 11, e.g., with 1,3,5-triazine or its derivatives, under suitable conditions to form hexahydro-1,3,5-triazine of formula 13;

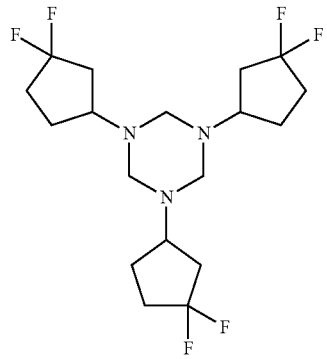

13 and (b) reacting the compound of formula 13 with a ketene silyl acetal of formula 14;

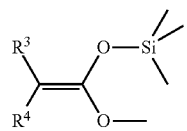

14 under suitable conditions to form the compound of formula 2a.

Still another aspect of this invention provides a process for preparing a compound of formula I-C:

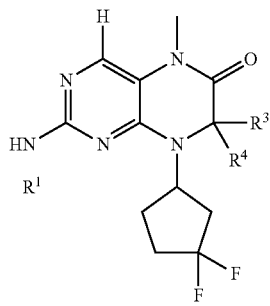

I-C

In formula I-C, R¹ is

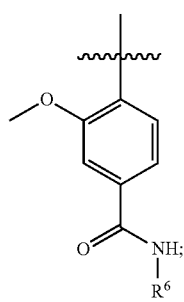

R⁶ is $C_{1-4}$ aliphatic or $C_{3-6}$ cycloaliphatic, and is optionally substituted with 1 or 2 halogen atoms (e.g., 2 fluorine atoms); and each of R³ and R⁴ is independently H, methyl, or ethyl; or R³ and R⁴, together with the atoms to which they are attached, form a cyclopropyl ring. This process includes the step of reacting a compound of formula 5C:

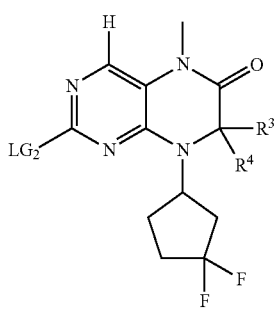

5C wherein $LG_2$ is a leaving group, with $H_2NR^1$ to form the compound of formula I-C.

In some embodiments, this process further includes the step of reacting a compound of formula 4C:

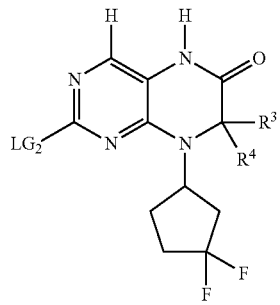

4C with Me-$LG_3$, wherein $LG_3$ is a leaving group capable of being displaced by an NH amide under suitable conditions, to form the compound of formula 5C In some other embodiments, the process of this invention further includes the step of reductive cyclization of a compound of formula 3C:

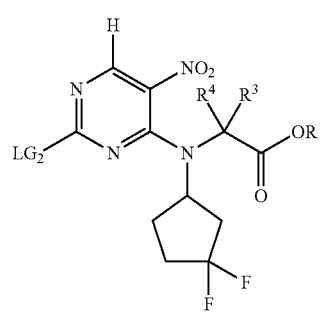

3C under suitable conditions to form a compound of formula 4C.

In some other embodiments, the process further includes cyclizing a compound of formula 3C-a:

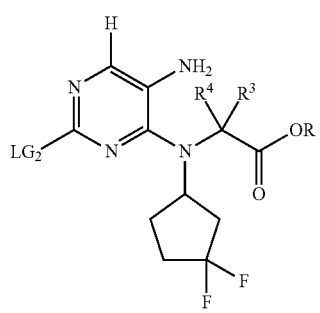

3C-a under cyclo-condensation conditions to form a compound of formula 4C.

In some other embodiments, the process further includes the step of reacting a compound of formula 3C:

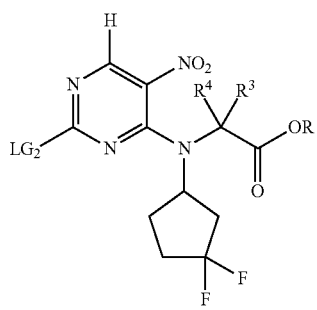

3C under suitable reduction conditions to form a compound of formula 3C-a.

In some other embodiments, the process further includes the steps of (a) reacting the compound of formula 3C-a with an alkylating agent under suitable conditions to form a compound of formula 3C-b;

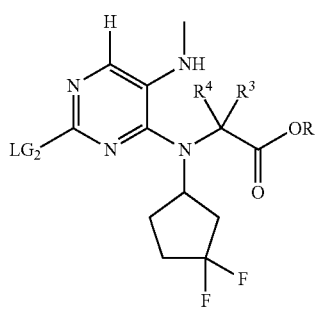

3C-b and (b) cyclizing the compound of formula 3C-b under suitable cyclo-condensation conditions to form a compound of formula 5C. Examples of suitable alkylating agents include alkyl halide.

In some other embodiments, the process further includes the step of reacting a compound of formula 2b:

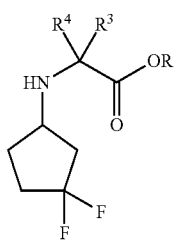

2b with a compound of formula 1:

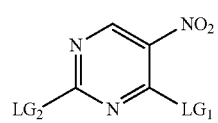

1 under suitable displacement conditions to form the compound of formula 3C.

In some other embodiments, the process further includes the step of reacting a compound of formula 11:

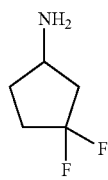

11 with a compound of formula 15:

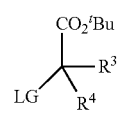

15 under suitable displacement conditions, to form the compound of formula 2b.

In yet another aspect, the present include provides a process for preparing a compound of formula 1-B:

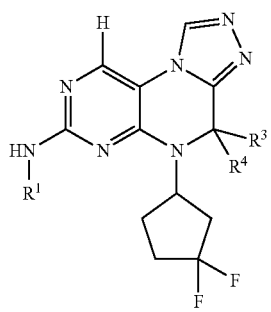

I-B

In formula I-B, $R^1$ is

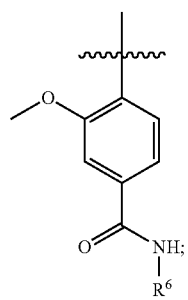

$R^6$ is $C_{1-4}$ aliphatic or $C_{3-6}$ cycloaliphatic, and is optionally substituted with 1 or 2 halogen atoms (e.g., 2 fluorine atoms); and each of R3 and R4 is independently H, methyl, or ethyl; or R3 and R4, together with the atoms to which they are attached, form a cyclopropyl ring. This process includes the step of reacting a compound of formula 10:

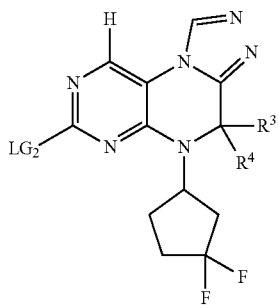

10 wherein LG$_2$ is a suitable leaving group, with H$_2$NR$^1$ under suitable conditions to form the compound of formula I-B.

In some other embodiments, the process further includes the step of reacting a compound of formula 9:

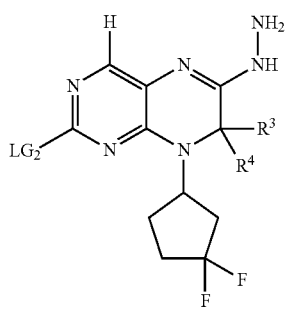

9 under suitable cyclization conditions known in the art for converting hydrazides into 1,2,4-triazoles, to form a compound of formula 10.

In some other embodiments, the process further includes the step of reacting a compound of formula 8:

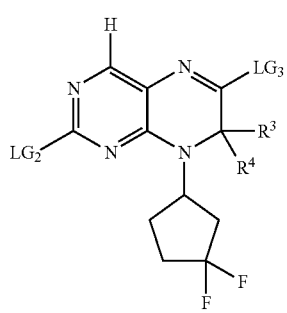

8 wherein LG$_3$ is a leaving group capable of being displaced by an NH amide under suitable conditions, with hydrazine to form the compound of formula 9.

In some other embodiments, the process further includes reacting a compound of formula 4C:

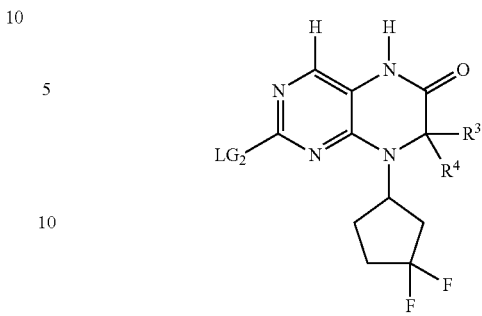

4C under suitable conditions known in the art for converting amides into activated amides, to form a compound of formula 8.

In some other embodiments of the process, R$^2$ and R$^5$, together with the atoms to which they are attached, form a 1,2,4-triazole.

Compounds of this invention include those described herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York (2001), the entire contents of which are hereby incorporated by reference.

As described herein, a specified number range of atoms includes any integer therein, including the upper and lower limits of the range. For example, a group having from 1 to 4 (or 1-4) atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched), branched, or cyclic substituted or unsubstituted hydrocarbon chain that is completely saturated or that contains one or more units of unsaturation that has a single point of attachment to the rest of the molecule.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

It should be understood that if the aliphatic is alkenyl or alkynyl, then the aliphatic group has at least 2 carbon atoms.

The term "cycloaliphatic" refers to a monocyclic $C_3$-$C_8$ hydrocarbon or bicyclic $C_7$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups. The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g., cycloaliphatic and heterocycles), can be linearly fused, bridged, or spirocyclic.

The term "heteroatom" means one or more of oxygen, sulfur, nitrogen, or phosphorus, (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR' (as in N-substituted pyrrolidinyl)).

The term "unsaturated", as used herein, means that a moiety has one or more units of unsaturation.

The term "nonaromatic", as used herein, describes rings that are either saturated or partially unsaturated.

The term "aromatic", as used herein, describes rings that are fully unsaturated.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F (fluorine), Cl (chlorine), Br (bromine), or I (iodine).

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired reactive sites in a multifunctional compound. In certain embodiments, a protecting group has one or more, or preferably all, of the following characteristics: (a) is added selectively to a functional group in good yield to give a protected substrate that is (b) stable to reactions occurring at one or more of the other reactive sites; and (c) is selectively removable in good yield by reagents that do not attack the regenerated, deprotected functional group. Exemplary protecting groups are detailed and provided by T. W. Greene et al. in "Protective Groups in Organic Synthesis", Third Edition, John Wiley & Sons, New York (1999) (and other editions of the book), the entire contents of which are hereby incorporated by reference. The term "nitrogen protecting group," as used herein, refers to an agents used to temporarily block one or more desired nitrogen reactive sites in a multifunctional compound. Certain exemplary nitrogen protecting groups are also detailed and provided by T. W. Greene et al., in Chapter 7 of "Protective Groups in Organic Synthesis", Third Edition, John Wiley & Sons, New York (1999), the entire contents of which are hereby incorporated by reference.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —$CO_2$—, —OC(O)—, —C(O) CO—, —C(O)—, —C(O)NR—, —C(=N—CN)—, —NRCO—, —NRC(O)O—, —$SO_2$NR—, —NR$SO_2$—, —NRC(O)NR—, —OC(O)NR—, —NR$SO_2$NR—, —SO—, or —$SO_2$—, wherein R is defined herein. Unless otherwise specified, the optional replacements form a chemically stable compound. Optional interruptions can occur both within the chain and at either end of the chain; i.e., both at the point of attachment and/or also at the terminal end. Two optional replacements can also be adjacent to each other within a chain so long as it results in a chemically stable compound. The optional interruptions or replacements can also completely replace all of the carbon atoms in a chain. For example, a $C_3$ aliphatic can be optionally interrupted or replaced by —NR—, —C(O)—, and —NR— to form —NRC(O)NR— (a urea).

Unless otherwise specified, if the replacement or interruption occurs at the terminal end, the replacement atom is bound to an H on the terminal end. For example, if —$CH_2CH_2CH_3$ were optionally interrupted with —O—, the resulting compound could be —$OCH_2CH_3$, —$CH_2OCH_3$, or —$CH_2CH_2OH$.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Unless otherwise stated, a substituent can freely rotate around any rotatable bonds. For example, a substituent drawn as

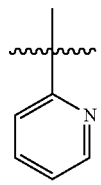 [SMILES: *c1ccccn1]

also represents

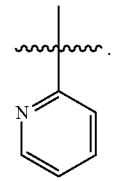 [SMILES: *c1ccccn1]

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$($C_{1-4}$alkyl)$_4$ salts. This invention also envisions the quaternization of any basic nitrogen-containing groups of the compounds disclosed herein. Water or oil-soluble or dispersible products may be obtained by such quaternization.

Base addition salts can be prepared by (1) reacting the purified compound in its acid form with a suitable organic or inorganic base, and (2) isolating the salt thus formed. Base addition salts include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

The following abbreviations are used:

PG protecting group
LG leaving group
DCM dichloromethane
Ac acetyl
DMF dimethylformamide
EtOAc ethyl acetate
DMSO dimethyl sulfoxide
MeCN acetonitrile
TCA trichloroacetic acid
ATP adenosine triphosphate
EtOH ethanol
Ph phenyl
Me methyl
Et ethyl
Bu butyl
DEAD diethylazodicarboxylate
HEPES 4-(2-hydroxyethyl)-1-piperazineethanesulfonic acid
BSA bovine serum albumin
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time In some embodiments, the compounds of this invention are represented in Table 1.

TABLE 1

I-1

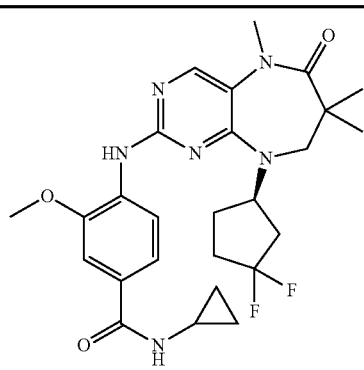

TABLE 1-continued

I-2

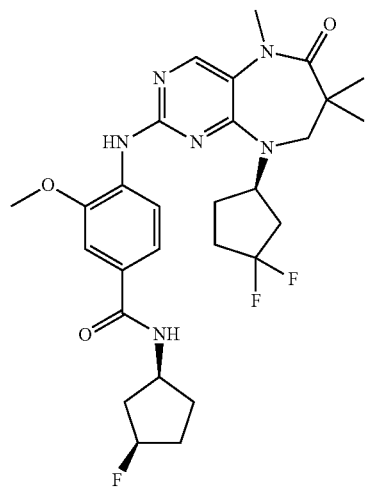

I-3

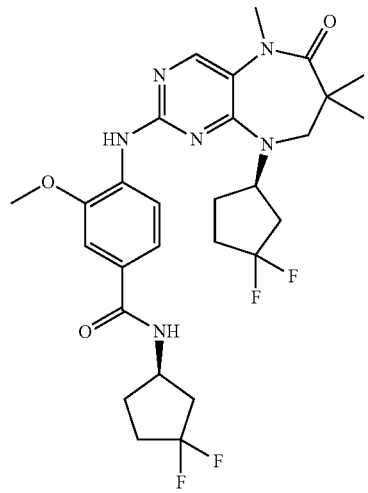

I-4

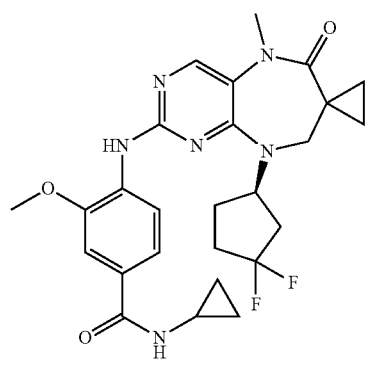 [SMILES: COc1cc(C(=O)NC2CC2)ccc1Nc1ncc2c(n1)N([C@@H]1CCC(F)(F)C1)CC1(CC1)C(=O)N2C]

TABLE 1-continued

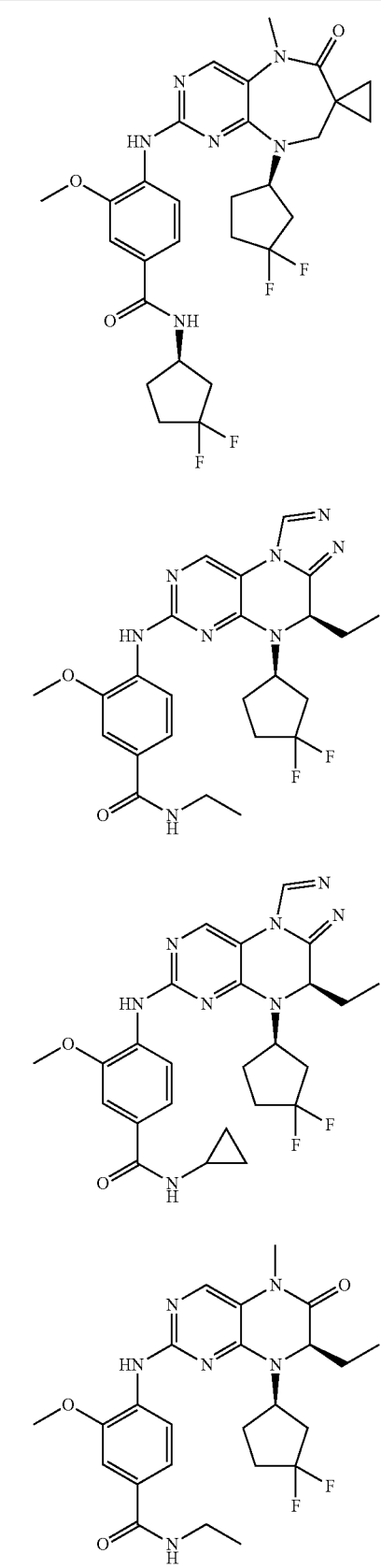

I-5

I-6

I-7

I-8

TABLE 1-continued

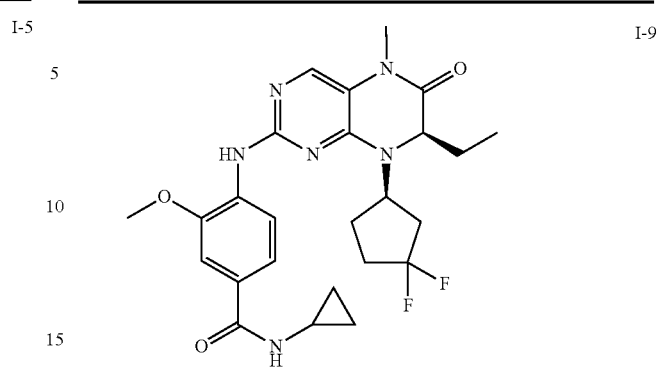

I-9

General Synthetic Methodology

The compounds of this invention may be prepared in general by methods such as those depicted in the general schemes below. Unless otherwise indicated, all variables in the following schemes are as defined herein.

In one method, the compounds of the invention wherein X is O may be prepared as illustrated in Scheme 1.

Scheme 1

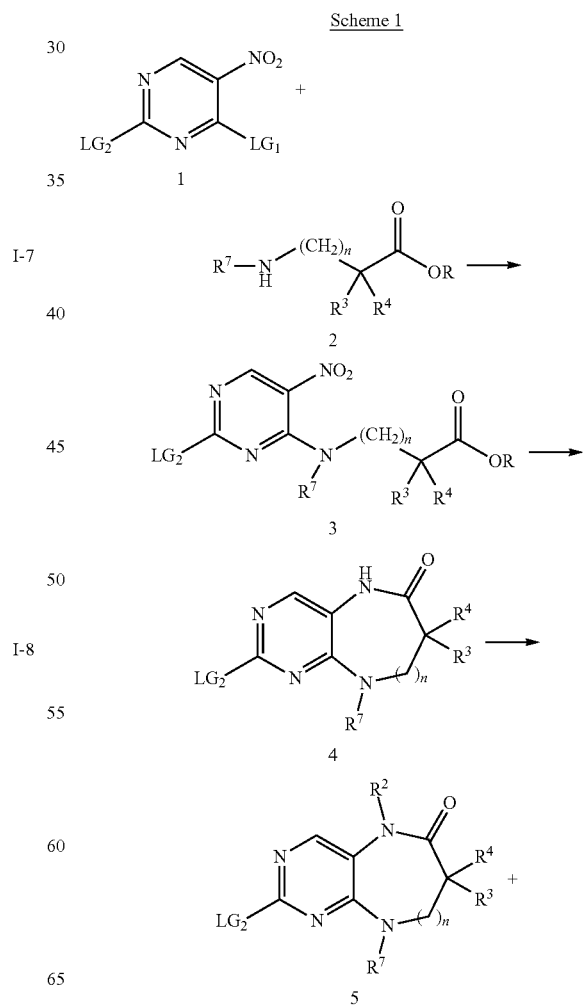

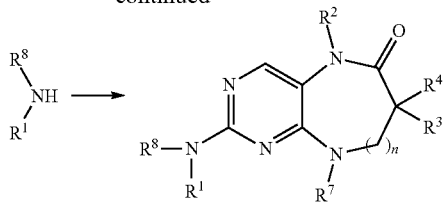

Referring to Scheme 1, the nitro pyrimidine 1, wherein $LG_1$ and $LG_2$ are, for example, chlorine, reacts with α- or β-aminoesters 2 (in which n is 0 or 1) to provide an adduct 3. Reduction of the nitro group under known conditions, followed by cyclization, provides bicyclic compound 4. The amide N—H may be functionalized by reaction with, for example, an alkyl halide in the presence of a strong base such as, for example, sodium hydride to provide compound 5. Reaction of compound 5 with $R^1R^8NH$, optionally in the presence of a palladium catalyst, provides a compound of formula 1.

An alternate method for synthesizing the compounds of this invention is illustrated in Scheme 2.

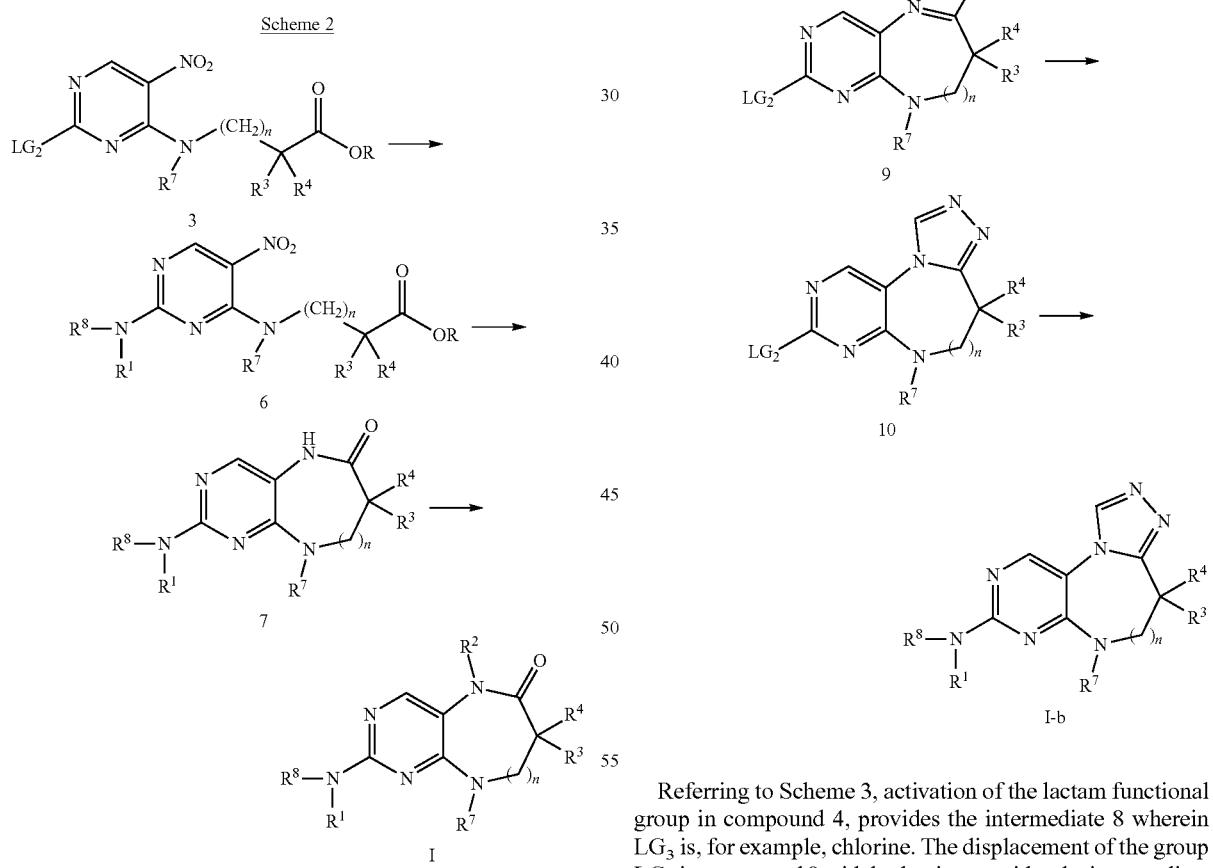

Referring to Scheme 2, compound 3 wherein $LG_2$ is, for example, chlorine, reacts with $R^1R^8NH$, optionally in the presence of a palladium catalyst, to provide compound 6. Reduction of the nitro group in compound 6 as previously described, followed by cyclization provides a bicyclic compound 7. The amide group in compound 7 is functionalized to provide compounds of formula I.

Illustrated below in Scheme 3 is a method for preparing compounds of this invention wherein X is —$NR^5$ and $R^5$ and $R^2$, together with the atoms to which they are attached, form a triazole ring.

Scheme 3

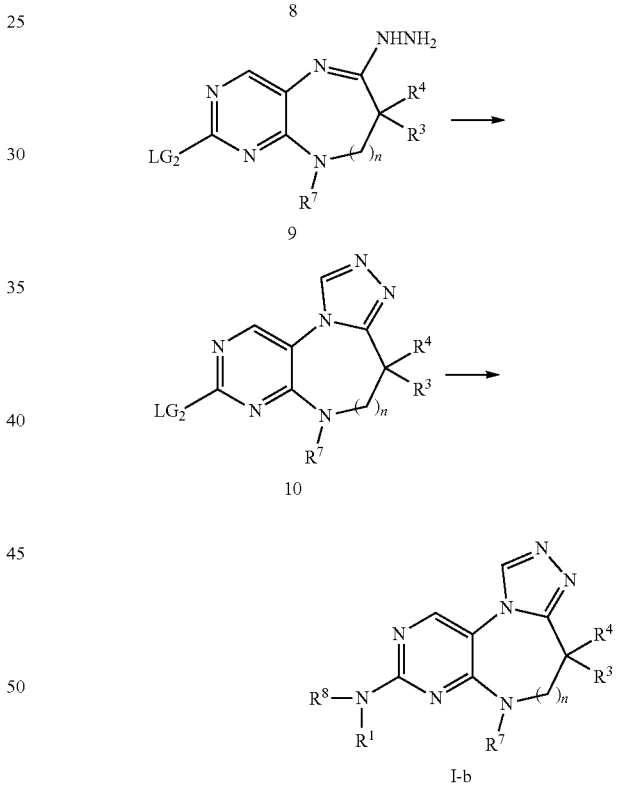

Referring to Scheme 3, activation of the lactam functional group in compound 4, provides the intermediate 8 wherein $LG_3$ is, for example, chlorine. The displacement of the group $LG_3$ in compound 8 with hydrazine provides the intermediate of formula 9. Reaction of compound 9 with an orthoformate ester (e.g., methyl orthoformate) provides the triazole intermediate 10. Reaction of compound 10 with $R^1R^8NH$ as previously described provides a compound of formula I-b.

Shown below in Scheme 4 is a method for preparing compounds of formula 2 wherein $R^7$ is 3,3-difluorocyclopentyl and n is 1, which are shown in the Scheme as formula 2a.

Scheme 4

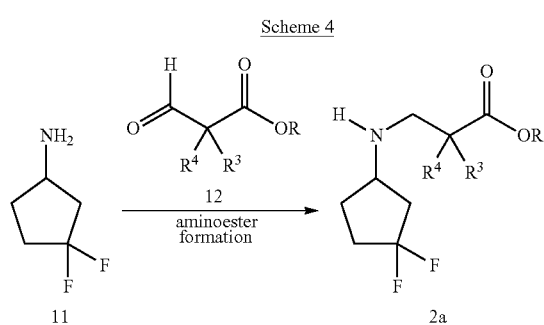

Referring to Scheme 4, 3,3-difluorocyclopentanamine 11 (described in WO 2007/062308 and WO 2007/062314) reacts with an aldehyde 12 under known reductive amination conditions to provide intermediates 2a. Suitable reductive amination conditions as used, e.g., in Eschweiler-Clarke Reaction, and in addition are described in literature. See, e.g., A. F. Abdel-Magid et al., J. Org. Chem., 1996, 61, 3849-3862; J. W. Bae et al., J. Chem. Soc., Perkin Trans. 1, 2000, 145-146; B. T. Cho et al., Tetrahedron, 2005, 61, 5725-5734; M. McLaughlin et al., Org. Lett., 2006, 8, 3307-3310; T. Mizuta et al., J. Org. Chem., 2005, 70, 2195-2199.

An alternative method for preparing intermediates of formula 2a is illustrated in Scheme 5.

Scheme 5

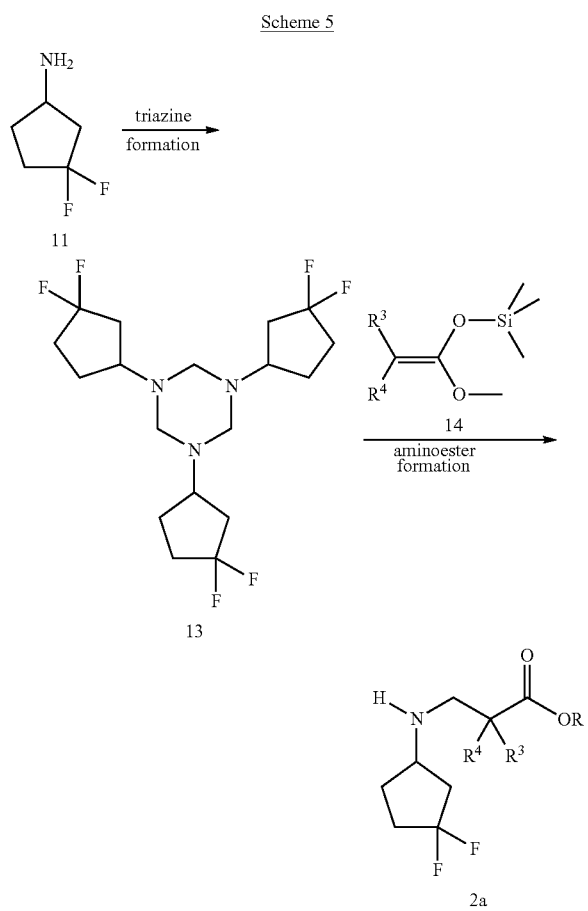

In Scheme 5, 3,3-difluorocyclopentanamine 11 reacts with formaldehyde in the presence of sodium hydroxide to provide the 1,3,5-triazine 13. Reaction of compound 13 with a ketene silyl acetal of formula 14 provides an intermediate of formula 2a.

Shown below in Scheme 6 is a method for preparing compound of formula 2 in which n is 0 (shown in the Scheme as formula 2b).

Scheme 6

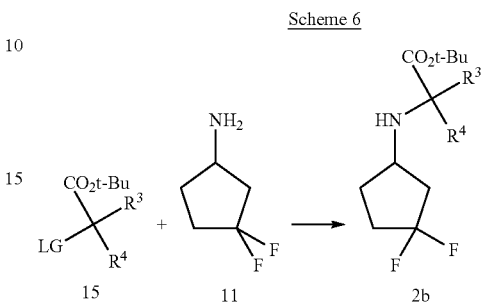

Referring to Scheme 6, a compound of formula 15 wherein LG is, for example, bromine, reacts with 3,3-difluorocyclopentanamine 11 to give an aminoester of formula 2b.

Another aspect of this invention provides compounds that are inhibitors of protein kinases, and thus are useful for the treatment of the diseases, disorders, or conditions (collectively "disorders") implicated by protein kinases, along with other uses described herein. Examples of such conditions include proliferative disorders, neurodegenerative disorders, autoimmune disorders, inflammatory disorders, or immunologically mediated disorders that are implicated or mediated by protein kinases (e.g., PLK1, pLK2, PLK3, or PLK4). Specific examples of such conditions include, but are not limited to, melanoma, myeloma, leukemia, lymphoma, neuroblastoma, or a cancer selected from colon, breast, gastric, ovarian, cervical, lung, central nervous system (CNS), renal, prostate, bladder, or pancreatic.

In another aspect of the present invention, pharmaceutically acceptable compositions are provided, wherein these compositions each comprise any of the compounds described herein, and optionally a pharmaceutically acceptable carrier, adjuvant or vehicle.

In certain embodiments of the compositions of this invention, these compositions each further comprise one or more additional therapeutic agents. Examples of such additional therapeutic agents include, but are not limited to, a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders. The additional therapeutic agent can be administered together with the compound or the pharmaceutical composition of as a single dosage form or separately from the compound or pharmaceutical composition as part of a multiple dosage form.

The present invention provides compounds and compositions that are useful as inhibitors of protein kinases. In some embodiments, the protein kinases are PLKs (e.g., PLK1, PLK2, PLK3, or PLK4). In some embodiments, PLK1.

As inhibitors of protein kinases, the compounds and compositions of this invention are particularly useful for treating or lessening the severity of a disease, condition, or disorder where a protein kinase is implicated in the disease, condition, or disorder. In one aspect, the present invention provides a method for treating or lessening the severity of a disease, condition, or disorder where a protein kinase is implicated in the disease state. In another aspect, the present invention provides a method for treating or lessening the severity of a kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said protein kinase inhibitor is a PLK inhibitor.

One aspect of the invention relates to a method of inhibiting protein kinase activity in a patient, which method comprises administering to the patient a compound of formula I, or a composition comprising said compound.

In some embodiments, said method is used to treat or prevent a condition selected from autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In some embodiments, said protein kinase in PLK. In other embodiments, said condition is selected from a proliferative disorder and a neurodegenerative disorder.

Depending upon the particular protein kinase-mediated conditions to be treated or prevented, additional drugs, which are normally administered to treat or prevent that condition, may be administered together with the inhibitors of this invention. For example, chemotherapeutic agents or other anti-proliferative agents may be combined with the protein kinase inhibitors of this invention to treat proliferative diseases.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

As inhibitors of protein kinases, the compounds and compositions of this invention are also useful in biological samples. One aspect of the invention relates to inhibiting protein kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention as an inhibitor of PLK1, PLK2, PLK3, and PLK4 are set forth in the Examples below.

One aspect of this invention provides compounds that are useful for the treatment of diseases, disorders, and conditions characterized by excessive or abonormal cell proliferation. Such diseases include, a proliferative or hyperproliferative disease, and a neurodegenerative disease.

Examples of proliferative and hyperproliferative diseases include, without limitation, cancer.

The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

For the avoidance of doubt, the term "cancer" also includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

In some embodiments, the compounds of this invention are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AML), chronic-myelogenous leukemia (CML), acute-promyelocytic leukemia (APL), and acute lymphocytic leukemia (ALL).

Examples of neurodegenerative diseases include, without limitation, Alzheimer's disease.

Another aspect of this invention provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

In some embodiments, said disease is a protein-kinase mediated condition. In some embodiments, said disease is a PLK-mediated disease.

The term "protein kinase-mediated condition", as used herein, means any disease or other deleterious condition in which a protein kinase plays a role. Such conditions include, without limitation, autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease.

The term "PLK-mediated condition", as used herein means any disease or other deleterious condition in which PLK plays a role. Such conditions include, without limitation, a proliferative or hyperproliferative disease, or a neurodegenerative disease.

In another aspect of the present invention, pharmaceutically acceptable compositions are provided, wherein these compositions comprise any of the compounds as described herein, and optionally comprise a pharmaceutically acceptable carrier, adjuvant or vehicle.

In certain embodiments, these compositions optionally further comprise one or more additional therapeutic agents.

For example, chemotherapeutic agents or other anti-proliferative agents may be combined with the compounds of this invention to treat proliferative diseases and cancer.

Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

As described herein, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention. In some embodiments, said protein kinase-mediated condition is a PLK-mediated condition.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. In a preferred embodiment, compounds of this invention are administered orally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In addition to the compounds of this invention, pharmaceutically acceptable derivatives or prodrugs of the compounds of this invention may also be employed in compositions to treat or prevent the above-identified disorders.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01 and 100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a protein kinase-mediated condition (in some embodiments, a PLK-mediated condition) comprising the step of administering to a patient one of the above-described pharmaceutical compositions. The term "patient", as used herein, means an animal, preferably a human.

In some embodiments, said method is used to treat or prevent a condition selected from a proliferative disorder, such as cancer, a neurodegenerative disorder, an autoimmune disorder, an inflammatory disorder, and an immunologically-mediated disorder. In some embodiments, said method is used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, cystic fibrosis, and viral disease, or any specific disease described above.

The compounds of this invention may be prepared in general by methods known to those skilled in the art. Those compounds may be analyzed by known methods, including but not limited to LCMS (liquid chromatography mass spectrometry) and NMR (nuclear magnetic resonance). Compounds of this invention may be also tested according to these examples. It should be understood that the specific conditions shown below are only examples, and are not meant to limit the scope of the conditions that can be used for making, analyzing, or testing the compounds of this invention. Instead, this

EXAMPLES

As used herein, the term "Rt(min)" refers to the HPLC retention time, in minutes, associated with the compound. Unless otherwise indicated, the HPLC method utilized to obtain the reported retention time is as follows:
Column: ACE C8 column, 4.6×150 mm
Gradient: 0-100% acetonitrile+methanol 50:50 (20 mM Tris phosphate)
Flow rate: 1.5 mL/minute
Detection: 225 nm.

Mass spec. samples were analyzed on a MicroMass Quattro Micro mass spectrometer operated in single MS mode with electrospray ionization. Samples were introduced into the mass spectrometer using chromatography.

$^1$H-NMR spectra were recorded at 400 MHz using a Bruker DPX 400 instrument. The following compounds of formula I were prepared and analyzed as follows.

Example 1

(R)—N-cyclopropyl-4-(9-(3,3-difluorocyclopentyl)-5,7,7-trimethyl-6-oxo-6,7,8,9-tetrahydro-5H-pyrimido[4,5-b][1,4]diazepin-2-ylamino)-3-methoxybenzamide

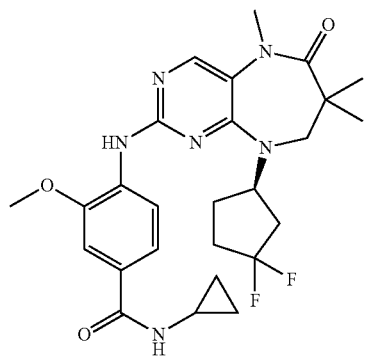

Step 1: tert-butyl (1R,3S)-3-hydroxycyclopentylcarbamate

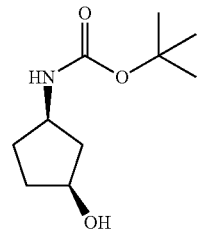

Di-tert-butyl dicarbonate (432 mg, 1.98 mmol) was added to a solution of (1S,3R)-3-aminocyclopentanol (200 mg, 1.98 mmol) and triethylamine (0.662 ml, 4.75 mmol) in dichloromethane (20 mL) at 0° C. After complete addition, the reaction mixture was allowed to warm up to room temperature and was stirred for 18 hours. The reaction mixture was concentrated under vacuo and purified on silica gel by flash column chromatography to give the required compound (380 mg, 95% yield).

$^1$H NMR (CDCl3, 400 MHz) δ 1.45 (9H, s), 1.64 (1H, br d), 1.78-1.96 (4H, m), 1.96-2.11 (2H, m), 4.05 (1H, br s), 4.39 (1H, br s).

Step 2: (R)-tert-butyl 3-oxocyclopentylcarbamate

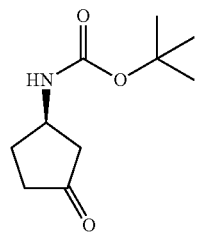

Dess-Martin periodinane (961 mg, 2.27 mmol) was added portionwise to a solution of tert-butyl (1R,3S)-3-hydroxycyclopentylcarbamate (380 mg, 1.89 mmol) in dichloromethane (10 mL) at 0° C. After complete addition, the reaction mixture was stirred for 1 hour at 0° C., then, allowed to warm up to room temperature and stirred for 18 hours. The reaction mixture was quenched with a 50/50 of a saturated aqueous solution of sodium bicarbonate and a saturated aqueous solution of sodium thiosulfate. The aqueous layer was extracted 3 times with dichloromethane. The combined organic layers were washed with brine, dried over magnesium sulfate and concentrated in vacuo. The residue was purified on silica gel by flash column chromatography to give the title compound (316 mg, 84% yield).

$^1$H NMR (CDCl$_3$, 400 MHz): δ 1.47 (9H, s), 1.01-1.13 (1H, m), 2.13 (1H, dd), 2.25 (1H, m), 2.31-2.44 (2H, m), 2.65 (1H, dd), 4.24 (1H, br s), 4.62 (1H, br s).

Step 3: (R)-tert-butyl 3,3-difluorocyclopentylcarbamate

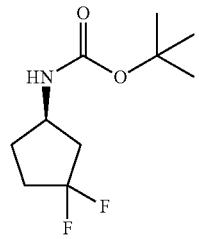

Deoxofluor® [bis(2-methoxyethyl)aminosulfur trifluoride, 0.574 ml, 3.12 mmol] was added dropwise to a solution of (R)-tert-butyl 3-oxocyclopentylcarbamate (310 mg, 1.56 mmol) in dichloromethane (8 mL) at 0° C. After complete addition, the reaction mixture was allowed to warm up to room temperature and stirred for 18 hours. The reaction mixture was poured slowly into an ice-cold saturated aqueous solution of sodium bicarbonate. The aqueous layer was extracted 3 times with dichloromethane. The combined organic layers were dried over magnesium sulfate and concentrated under vacuo. The residue was purified on silica gel by flash column chromatography to give the title compound (226 mg, 66% yield).

$^1$H NMR (DMSO-$d_6$, 400 MHz): δ 1.46 (9H, s), 1.61-1.74 (1H, m), 1.90-2.32 (4H, m), 2.52 (1H, dq), 4.18 (1H, br s), 4.65 (1H, br s).

Step 4: (R)-3,3-difluorocyclopentanamine hydrochloride

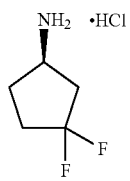

Hydrochloric acid (4M in dioxane, 60 mL) was added to a solution of (R)-tert-butyl 3,3-difluorocyclopentylcarbamate (4.61 g, 20.8 mmol) in dioxane (40 mL) at 0° C. After complete addition, the reaction mixture was allowed to warm to room temperature and stirred for 2 hours. The solvent was removed in vacuo and the residue was triturated with diethylether to afford the title compound as an off-white solid (2.68 g, 82% yield).

$^1$H NMR (CDCl$_3$, 400 MHz): δ 1.76-1.88 (1H, m), 2.10-2.40 (4H, m), 2.45-2.60 (1H, m), 3.68 (1H, quint), 8.33 (3H, s).

Step 5: 1,3,5-tris((R)-3,3-difluorocyclopentyl)-1,3,5-triazinane

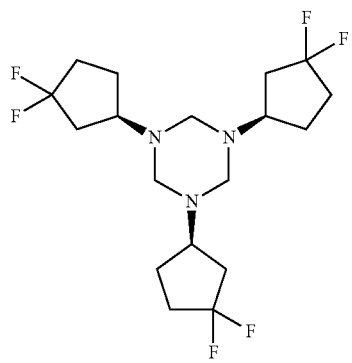 [SMILES: FC1(F)CC[C@@H](N2CN([C@@H]3CCC(F)(F)C3)CN([C@@H]3CCC(F)(F)C3)C2)C1]

(R)-3,3-difluorocyclopentanamine hydrochloride (2.68 g, 17 mmol) in ethanol (17 mL) was cooled to 0° C. Aqueous sodium hydroxide (2 M, 8.5 ml, 17 mmol) was added followed by 37% formaldehyde (1.38 ml, 17 mmol) were added dropwise. After complete addition, the reaction mixture was stirred for 15 minutes at 0° C. then allowed to warm to room temperature and stir for a further hour. The title compound was isolated as an white solid by filtration (1.75 g, 77% yield).

$^1$H NMR (CDCl$_3$, 400 MHz): δ 1.60-1.75 (3H, m), 1.90-2.15 (9H, m), 2.18-2.43 (6H, m), 3.11 (3H, br s), 3.39 (6H, br s).

Step 6: (R)-methyl 3-(3,3-difluorocyclopentylamino)-2,2-dimethylpropanoate

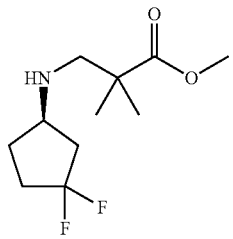 [SMILES: COC(=O)C(C)(C)CN[C@@H]1CCC(F)(F)C1]

Triflic acid (58 μL, 0.66 mmol) was added to a solution of 1,3,5-tris((R)-3,3-difluorocyclopentyl)-1,3,5-triazinane (1.75 g, 4.38 mmol) and 1-methoxy-2-methyl-1-(trimethylsiloxy)propene (2.29 g, 13.14 mmol) in dichloromethane (40 mL) at 0° C. After complete addition, the reaction mixture was allowed to warm up to room temperature and stirred for 2 hours. The reaction mixture was diluted with dichloromethane, washed with an aqueous saturated solution of sodium bicarbonate and brine. The organic layer was dried over magnesium sulfate and concentrated in vacuo. The residue was purified on silica gel by flash column chromatography to afford the title compound as oil (2.72 g, 88% yield).

$^1$H NMR (CDCl$_3$, 400 MHz): δ 1.05 (6H, s), 1.30-1.56 (3H, m), 1.72 (1H, dq), 1.80-1.95 (1H, m), 2.00-2.28 (2H, m), 2.49 (2H, dd), 3.09 (1H, quint), 3.54 (3H, s).

Step 7: (R)-methyl 3-((2-chloro-5-nitropyrimidin-4-yl)(3,3-difluorocyclopentyl)amino)-2,2-dimethylpropanoate

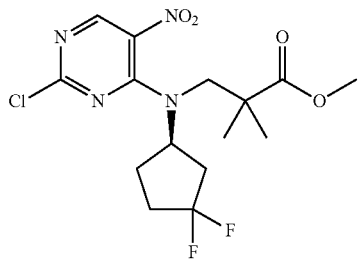 [SMILES: COC(=O)C(C)(C)CN(c1nc(Cl)ncc1[N+](=O)[O-])[C@@H]1CCC(F)(F)C1]

2,4-Dichloro-5-nitropyrimidine (2.18 g, 11.25 mmol) was added to a mixture of (R)-methyl 3-(3,3-difluorocyclopentylamino)-2,2-dimethylpropanoate (2.65 g, 11.25 mmol) and sodium bicarbonate (3.78 g, 44.98 mmol) in dichloromethane (10 mL) and petroleum ether (40 mL). The reaction mixture was stirred at room temperature for 18 hours. The reaction mixture was diluted with dichloromethane and dried over magnesium sulfate. The solids were filtered off, rinsing with more dichloromethane. The mother liquors were adsorbed on silica gel and concentrated in vacuo. The residue was purified by flash column chromatography to afford the title compound as yellow solid (2.74 g, 62% yield).

¹H NMR (CDCl₃, 400 MHz): δ 1.23 (6H, s), 1.90-2.07 (2H, m), 2.11-2.40 (3H, m), 2.40-2.55 (1H, m), 3.70 (3H, s), 3.72-3.84 (3H, m), 8.84 (1H, s); MS (ES+) 393.

Step 8: (R)-2-chloro-9-(3,3-difluorocyclopentyl)-7,7-dimethyl-8,9-dihydro-5H-pyrimido[4,5-b][1,4]diazepin-6(7H)-one

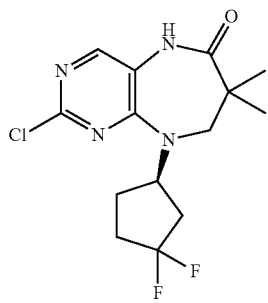 [SMILES: CC1(C)CN([C@@H]2CCC(F)(F)C2)c2nc(Cl)ncc2NC1=O]

A mixture of (R)-methyl 3-((2-chloro-5-nitropyrimidin-4-yl)(3,3-difluorocyclopentyl)amino)-2,2-dimethylpropanoate (2.74 g, 6.98 mmol) and iron powder (0.799 g, 14.31 mmol) in glacial acetic acid (30 mL) was heated to 70° C. for 2 hours. The reaction mixture was filtered hot and the cake was further washed with acetic acid. The mother liquors were concentrated in vacuo. The residue was taken up in a 15% solution of methanol in dichloromethane and filtered through a pad of silica gel rinsing with more methanol-dichloromethane solution. The filtrates were concentrated in vacuo. The residue was triturated with methanol and the solid was filtered to afford the title compound as an off-white solid (1.67 g, 72% yield).

¹H NMR (CDCl₃, 400 MHz): δ 1.30 (6H, s), 1.89 (1H, m), 2.03-2.23 (3H, m), 2.30-2.44 (1H, m), 2.48-2.64 (1H, m), 3.36 (2H, s), 5.52 (1H, quint), 7.73 (1H, s), 7.86 (1H, s); MS (ES+) 331, (ES−) 329.

Step 9: (R)-2-chloro-9-(3,3-difluorocyclopentyl)-5,7,7-trimethyl-8,9-dihydro-5H-pyrimido[4,5-b][1,4]diazepin-6(7H)-one

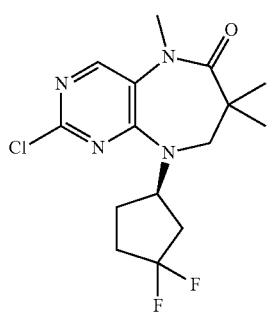 [SMILES: CN1C(=O)C(C)(C)CN([C@@H]2CCC(F)(F)C2)c2nc(Cl)ncc21]

60% Sodium hydride in mineral oil (0.210 g, 5.24 mmol) was added to a mixture of (R)-2-chloro-9-(3,3-difluorocyclopentyl)-7,7-dimethyl-8,9-dihydro-5H-pyrimido[4,5-b][1,4]diazepin-6(7H)-one (1.65 g, 4.99 mmol) and methyl iodide (0.34 ml, 5.49 mmol) in dimethylacetamide (18 mL). The reaction mixture was stirred at room temperature for 25 minutes. Ice was added to the reaction mixture and the resultant precipitate collected and rinsed with water. The solid was dried in a pistol in vacuo for 3 hours. The title compound was obtained as a white solid (1.68 g, 98% yield).

¹H NMR (DMSO-d₆, 400 MHz): δ 1.09 (6H, s), 1.87-2.22 (3H, m), 2.22-2.48 (3H, m), 3.19 (3H, s), 3.49 (2H, s), 5.26 (1H, quint), 8.12 (1H, s).

MS (ES+) 345.

Step 10: (R)—N-cyclopropyl-4-(9-(3,3-difluorocyclopentyl)-5,7,7-trimethyl-6-oxo-6,7,8,9-tetrahydro-5H-pyrimido[4,5-b][1,4]diazepin-2-ylamino)-3-methoxybenzamide

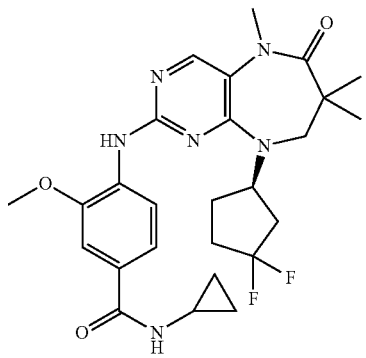

Concentrated hydrochloric acid (52 µl) was added to a mixture of (R)-2-chloro-9-(3,3-difluorocyclopentyl)-5,7,7-trimethyl-8,9-dihydro-5H-pyrimido[4,5-b][1,4]diazepin-6(7H)-one (100 mg, 0.29 mmol) and 4-amino-N-cyclopropyl-3-methoxybenzamide (90 mg, 0.44 mmol) in ethanol (1.4 mL) and water (5.2 mL). The reaction mixture was heated to 85° C. and stirred for 48 hours. The reaction mixture was concentrated in vacuo. The residue was dissolved in ethyl acetate, washed with an aqueous saturated solution of sodium bicarbonate and brine. The organic layer was dried over magnesium sulfate and concentrated in vacuo. The residue was purified on silica gel by flash column chromatography to afford the title compound as a white solid (83 mg, 56% yield).

Step 11: Mesylate Salt Formation (R)—N-cyclopropyl-4-(9-(3,3-difluorocyclopentyl)-5,7,7-trimethyl-6-oxo-6,7,8,9-tetrahydro-5H-pyrimido[4,5-b][1,4]diazepin-2-ylamino)-3-methoxybenzamide (83 mg, 0.16 mmol) was dissolved in hot (50° C.) methanol (4 mL) and treated with methane sulfonic acid (10.5 µL, 0.16 mmol), the mixture was evaporated under reduced pressure and azeotroped three times with diethyl ether. The residue was triturated with ether and filtered to give the methane sulfonate salt (69 mg, 71% yield).

¹H NMR (DMSO-d₆, 400 MHz): δ 0.54-0.61 (2H, m), 0.68-0.75 (2H, m), 1.14 (6H, d), 1.98-2.18 (3H, m), 2.28-2.46 (3H, m), 2.31 (3H, s), 2.80-2.86 (1H, m), 3.18 (3H, s), 3.56 (2H, s), 3.94 (3H, s), 5.34 (1H, dt), 7.49 (1H, d), 7.54 (1H, s), 8.03 (1H, d), 8.05 (1H, s), 8.41 (1H, d), 9.03 (1H, br s).

MS (ES+) 515, (ES−) 513.

Other compounds of formula I of this invention have been prepared via a sequence similar to the one described in Example 1.

Example 2

4-(9-((R)-3,3-difluorocyclopentyl)-5,7,7-trimethyl-6-oxo-6,7,8,9-tetrahydro-5H-pyrimido[4,5-b][1,4]diazepin-2-ylamino)-N-((1R,3R)-3-fluorocyclopentyl)-3-methoxybenzamide

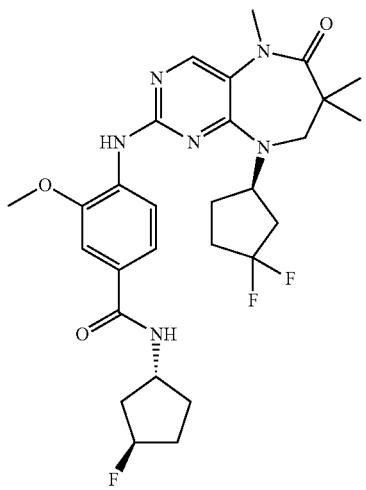

$^1$H NMR (DMSO-d$_6$, 400 MHz) δ 1.10 (6H, d), 1.55-2.40 (12H, m), 3.20 (3H, s), 3.45 (2H, s), 3.95 (3H, s), 4.45 (1H, sext), 5.20 (0.5H, s), 5.35 (0.5H, s), 5.40 (1H, quint), 7.45 (1H, d), 7.50 (1H, s), 7.80 (1H, s), 8.05 (1H, s), 8.25 (1H, d), 8.35 (1H, d).

MS (ES+) 561, (ES−) 559.

Example 3

N-((R)-3,3-difluorocyclopentyl)-4-(9-((R)-3,3-difluorocyclopentyl)-5,7,7-trimethyl-6-oxo-6,7,8,9-tetrahydro-5H-pyrimido[4,5-b][1,4]diazepin-2-ylamino)-3-methoxybenzamide

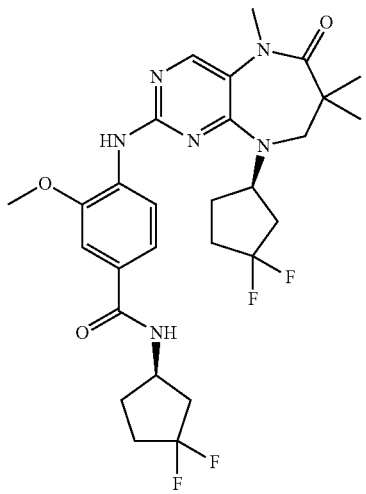

$^1$H NMR (DMSO-d$_6$, 400 MHz): δ 1.10 (6H, d), 1.80-2.50 (12H, m), 3.20 (3H, s), 3.45 (2H, s), 3.95 (3H, s), 4.45 (1H, sextet), 5.40 (1H, quintet), 7.45 (1H, d), 7.50 (1H, s), 7.80 (1H, s), 8.05 (1H, s), 8.35 (1H,d), 8.45 (1H,d).

MS (ES+) 579, (ES−) 577.

Example 4

(R)—N-cyclopropyl-4-(9'-(3,3-difluorocyclopentyl)-5'-methyl-6'-oxo-5',6',8',9'-tetrahydrospiro[cyclopropane-1,7'-pyrimido[4,5-b][1,4]diazepine]-2'-ylamino)-3-methoxybenzamide

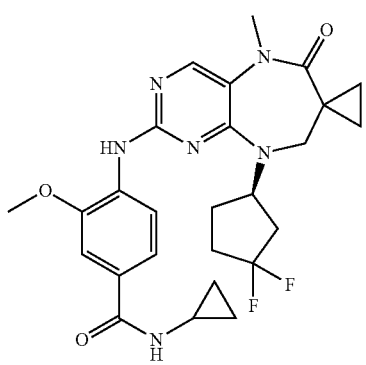 [SMILES: COc1cc(C(=O)NC2CC2)ccc1Nc1ncc2c(n1)N([C@@H]1CCC(F)(F)C1)CC1(CC1)C(=O)N2C]

Step 1: methyl 1-formylcyclopropanecarboxylate

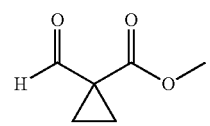

Dimethyl cyclopropane-1,1-dicarboxylate (6.90 ml, 50 mmol) was dissolved in dichloromethane (100 mL) and cooled to −78° C. DIBAL (1.0 M in DCM, 100 ml, 100 mmol) was added slowly over a period of 30 minutes. The reaction mixture was stirred for 6.5 hours at −78° C. then treated carefully with an aqueous saturated solution of ammonium chloride (16 mL) followed by HCl (1.0 M, 20 mL). The reaction was allowed to warm to room temperature over the weekend. The solids were filtered off and washed with DCM. The filtrate was washed with brine, dried over magnesium sulfate and the solvent removed under reduced pressure (200 mbar at rt). The crude product was purified on silica gel by flash column chromatography to afford the desired compound as a 45% w/w solution in EtOAc/DCM/ether as judged by $^1$H NMR (3.295 g).

$^1$H NMR (CDCl$_3$, 400 MHz): δ 1.58-1.63 (2H, m), 1.64-1.70 (2H, m), 3.81 (3H, s), 10.38 (1H, s).

Step 2: (R)-methyl 1-((3,3-difluorocyclopenty-lamino)methyl)cyclopropanecarboxylate

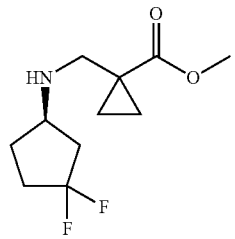 [SMILES: COC(=O)C1(CN[C@@H]2CCC(F)(F)C2)CC1]

Methyl 1-formylcyclopropanecarboxylate (45% w/w, 3.205 g, 11.26 mmol) and (R)-3,3-difluorocyclopentanamine hydrochloride (1.774 g, 11.26 mmol) were dissolved in dichloromethane (20 mL) at 0° C. under nitrogen. To this solution was added sodium acetate (0.923 g, 11.26 mmol) followed by sodium triacetoxyborohydride (3.46 g, 16.32 mmol). The reaction mixture was allowed to warm up to room temperature overnight. The reaction mixture was quenched with a saturated aqueous solution of sodium bicarbonate and stirred at room temperature for a further 10 minutes. The aqueous layer was extracted 3 times with dichloromethane. The combined organic layers were washed with brine, dried over magnesium sulfate and concentrated under vacuo. The residue was purified on silica gel by flash column chromatography to give the required compound (2.631 g, quantitative yield).

$^1$H NMR (CDCl$_3$, 400 MHz): δ 0.79-0.82 (2H, m), 1.25-1.29 (2H, m), 1.55-1.61 (1H, m), 1.82-2.08 (4H, m), 2.12-2.39 (2H, m), 2.67 (2H, dd), 3.26 (1H, quint), 3.65 (3H, s).

Step 3: (R)-methyl 1-(((2-chloro-5-nitropyrimidin-4-yl)(3,3-difluorocyclopentyl)amino)methyl)cyclopropane-carboxylate

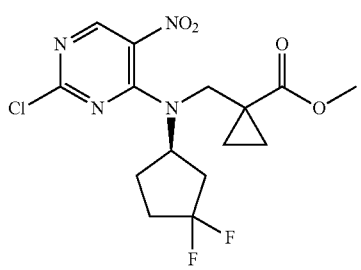 [SMILES: COC(=O)C1(CN(c2nc(Cl)ncc2[N+](=O)[O-])[C@@H]2CCC(F)(F)C2)CC1]

2,4-Dichloro-5-nitropyrimidine (2.16 g, 11.15 mmol) was added to a mixture of (R)-methyl 1-((3,3-difluorocyclopentylamino)methyl)cyclopropanecarboxylate (2.6 g, 11.15 mmol) and sodium bicarbonate (3.75 g, 44.64 mmol) in dichloromethane (15 mL) and petroleum ether (60 mL). The reaction mixture was stirred at room temperature for 18 hours. The reaction mixture was diluted with dichloromethane and dried over magnesium sulfate. The solids were filtered off, rinsing with more dichloromethane. The mother liquors were adsorbed on silica gel and concentrated in vacuo. The residue was purified by flash column chromatography to afford the desired product as a yellow solid (3.974 g, 91% yield).

$^1$H NMR (CDCl$_3$, 400 MHz): δ 0.96-1.05 (2H, m), 1.40-1.48 (2H, m), 2.06-2.25 (3H, m), 2.34-2.78 (3H, m), 3.53 (2H, dd), 3.59 (3H, s), 4.04 (1H, quint), 8.84 (1H, s).

MS (ES+) 391.

Step 4: (R)-2'-chloro-9'-(3,3-difluorocyclopentyl)-8',9'-dihydrospiro[cyclopropane-1,7'-pyrimido[4,5-b][1,4]diazepin]-6'(5'H)-one

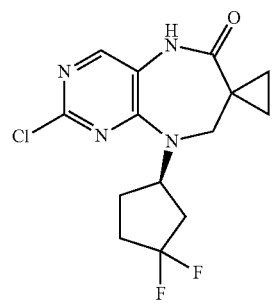 [SMILES: O=C1Nc2cnc(Cl)nc2N([C@@H]2CCC(F)(F)C2)CC12CC2]

A mixture of (R)-methyl 1-(((2-chloro-5-nitropyrimidin-4-yl)(3,3-difluorocyclopentyl)amino)methyl)cyclopropane-carboxylate (3.90 g, 9.98 mmol) and iron powder (1.143 g, 20.46 mmol) in glacial acetic acid (50 mL) was heated to 70° C. for 2 hours. The reaction mixture was filtered hot and the cake was further washed with acetic acid. The mother liquors were concentrated in vacuo. The residue was taken up in a 15% solution of methanol in dichloromethane and filtered through a path of silica gel rinsing with more methanol-dichloromethane solution. The mother liquors were concentrated in vacuo. The residue was triturated with methanol and the solid was filtered to afford the desired compound as a light pink solid (1.953 g, 60% yield).

$^1$H NMR (CDCl$_3$, 400 MHz): δ 0.87-0.95 (2H, m), 1.14-1.20 (2H, m), 1.75-1.86 (1H, m), 1.92-2.40 (5H, m), 3.48 (2H, dd), 5.01 (1H, quint), 7.80 (1H, s), 9.92 (1H, s).

MS (ES+) 329, (ES−) 327.

Step 5: (R)-2'-chloro-9'-(3,3-difluorocyclopentyl)-5'-methyl-8',9'-dihydrospiro[cyclopropane-1,7'-pyrimido[4,5-b][1,4]diazepin]-6'(5'H)-one

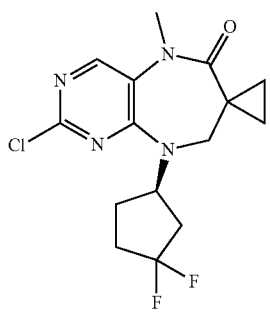 [SMILES: CN1C(=O)C2(CC2)CN([C@@H]2CCC(F)(F)C2)c2nc(Cl)ncc21]

60% sodium hydride in mineral oil (0.25 g, 6.23 mmol) was added to a mixture of (R)-2'-chloro-9'-(3,3-difluorocyclopentyl)-8',9'-dihydrospiro[cyclopropane-1,7'-pyrimido[4,5-b][1,4]diazepin]-6'(5'H)-one (1.95 g, 5.94 mmol) and methyl iodide (0.41 ml, 6.53 mmol) dimethylacetamide (20 mL). The reaction mixture was stirred at room temperature for 25 minutes. Ice was added to the reaction mixture. A solid crashed out and was filtered off, rinsing with water. The solid was dried in a pistol under vacuo for 3 hours. The compound was obtained as a light pink solid (1.863 g, 92% yield).

$^1$H NMR (DMSO-d$_6$, 400 MHz): δ 0.70-0.73 (2H, m), 0.90-0.96 (2H, m), 1.77-1.92 (1H, m), 2.00-2.45 (5H, m), 3.17 (3H, s), 3.59 (2H, dd), 4.89 (1H, quint), 8.12 (1H, s).

MS (ES+) 343.

Step 6: (R)—N-cyclopropyl-4-(9'-(3,3-difluorocyclopentyl)-5'-methyl-6'-oxo-5',6',8',9'-tetrahydrospiro[cyclopropane-1,7'-pyrimido[4,5-b][1,4]diazepine]-2'-ylamino)-3-methoxybenzamide

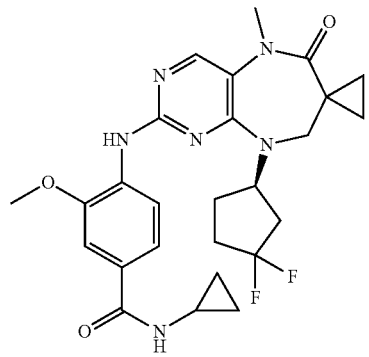 [SMILES: COc1cc(C(=O)NC2CC2)ccc1Nc1ncc2c(n1)N([C@@H]1CCC(F)(F)C1)CC1(CC1)C(=O)N2C]

Concentrated hydrochloric acid (45 µl) was added to a mixture of (R)-2'-chloro-9'-(3,3-difluorocyclopentyl)-5'-methyl-8',9'-dihydrospiro[cyclopropane-1,7'-pyrimido[4,5-b][1,4]diazepin]-6'(5'H)-one (100 mg, 0.29 mmol) and 4-amino-N-cyclopropyl-3-methoxybenzamide (90 mg, 0.44 mmol) in ethanol (1.4 mL) and water (5.2 mL). The reaction mixture was heated to 85° C. and stirred for 18 hours. The reaction mixture was concentrated in vacuo. The residue was taken up with ethyl acetate, washed with an aqueous saturated solution of sodium bicarbonate and brine. The organic layer was dried over magnesium sulfate and concentrated in vacuo. The residue was purified on silica gel by flash column chromatography to afford the desired compound as a white solid (49 mg, 33% yield).

$^1$H NMR (DMSO-d$_6$, 400 MHz): δ 0.53-0.60 (2H, m), 0.67-0.75 (4H, m), 0.82-0.95 (2H, m), 1.84-1.91 (1H, m), 2.04-2.31 (4H, m), 2.39-2.51 (1H, m), 2.81 (1H, m), 3.17 (3H, s), 3.51 (2H, dd), 3.93 (3H, s), 5.00 (1H, quint), 7.44 (1H, d), 7.47 (1H, s), 7.80 (1H, s), 8.04 (1H, s), 8.29-8.34 (2H, m).

MS (ES+) 513, (ES−) 511.

Example 5

N-((R)-3,3-difluorocyclopentyl)-4-(9'-((R)-3,3-difluorocyclopentyl)-5'-methyl-6'-oxo-5',6',8',9'-tetrahydrospiro[cyclopropane-1,7'-pyrimido[4,5-b][1,4]diazepine]-2'-ylamino)-3-methoxybenzamide

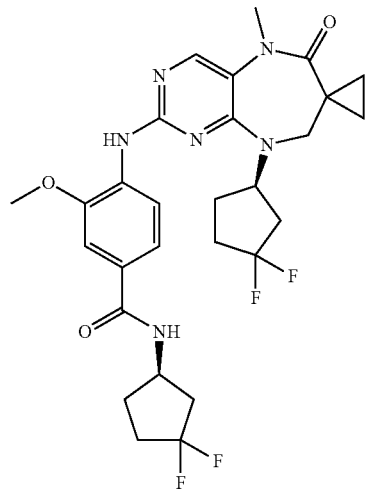 [SMILES: COc1cc(C(=O)N[C@@H]2CCC(F)(F)C2)ccc1Nc1ncc2c(n1)N([C@@H]1CCC(F)(F)C1)CC1(CC1)C(=O)N2C]

This compound was analyzed as a free base.

$^1$H NMR (DMSO-d$_6$, 400 MHz): δ 0.65-0.73 (2H, m), 0.82-0.96 (2H, m), 1.80-1.93 (2H, m), 2.04-2.30 (8H, m), 2.40-2.56 (2H, m), 3.17 (3H, s), 3.52 (2H, dd), 3.95 (3H, s), 4.43 (1H, dt), 5.01 (1H, quint), 7.47 (1H, d), 7.50 (1H, s), 7.82 (1H, s), 8.05 (1H, s), 8.34 (1H, d), 8.41 (1H, d).

MS (ES+) 577, (ES−) 575.

Example 6

4-((R)-5-((R)-3,3-difluorocyclopentyl)-4-ethyl-4,5-dihydro-[1,2,4]triazolo[4,3-f]pteridin-7-ylamino)-N-ethyl-3-methoxybenzamide

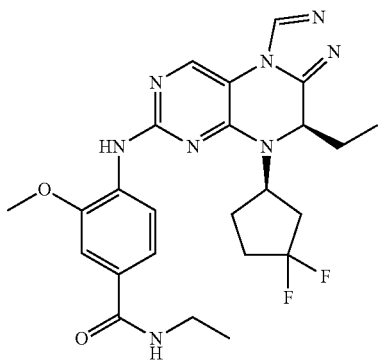 [SMILES: CCNC(=O)c1ccc(Nc2ncc3c(n2)N([C@@H]2CCC(F)(F)C2)[C@H](CC)C(=N)N3C=N)c(OC)c1]

Step 1: (S)-tert-butyl 2-(trifluoromethylsulfonyloxy)butanoate

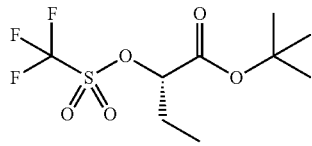 [SMILES: CC[C@H](OS(=O)(=O)C(F)(F)F)C(=O)OC(C)(C)C]

A solution of tert-butyl (s)-2-hydroxybutyrate (1.0 g, 6.242 mmol) in dichloromethane (30 mL), cooled down to 0° C., was treated dropwise with 2,6-lutidine (2.0 mL). The resultant solution was then treated dropwise with triflic anhydride (3.346 g, 1.995 ml, 11.86 mmol) added over 2-3 minutes. The reaction mixture was stirred at 0° C. for 40 minutes, then poured onto a mixture of brine (70 mL) and 1 M HCl (35 mL), extracted further with dichloromethane, dried over magnesium sulfate and concentrated under reduced pressure at room temperature to give a pale brown oil (2.6 g). The crude mixture was redissolved in dichloromethane and washed further with a 2:1 solution of saturated aqueous brine and 1 M HCl (2×20 mL) then brine, dried over magnesium sulfate and concentrated at room temperature to give pale brown oil (1.772 g, 97% yield).

¹H NMR (CDCl3, 400 MHz): δ 1.08 (3H, t), 1.53 (9H, s), 2.00-2.09 (2H, m), 4.97 (1H, dd).

Step 2: (R)-tert-butyl 2-((R)-3,3-difluorocyclopentyl amino)butanoate

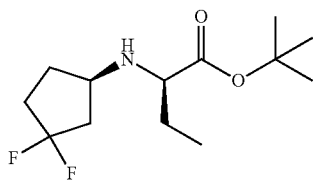 [SMILES: CC[C@@H](N[C@@H]1CCC(F)(F)C1)C(=O)OC(C)(C)C]

(R)-3,3-difluorocyclopentanamine hydrochloride (1.888 g, 11.98 mmol) in water (4 mL) was basified with potassium carbonate and extracted with dichloromethane (15 times) (total 50 mL). The solution was dried over magnesium sulfate, filtered, and added onto (S)-tert-butyl 2-(trifluoromethylsulfonyloxy)butanoate (1.75 g, 5.988 mmol). Dimethylsulfoxide (2 mL) was added and the mixture was concentrated at room temperature under 280 mbar (down to 8 mL volume). The resultant solution was transferred into a glass pressure tube and heated at 60° C. overnight. The resultant mixture was diluted with ethyl acetate and washed with an aqueous saturated solution of bicarbonate, dilute brine and dried over magnesium sulfate. The residue was purified on silica gel by flash column chromatography to afford the desired compound as colourless oil (1.17 g, 74% yield).

¹H NMR (CDCl3, 400 MHz): δ 0.94 (3H, t), 1.49 (9H, s), 1.54-1.67 (3H, m), 1.82-2.07 (3H, m), 2.21-2.40 (2H, m), 3.00 (1H, t), 3.22 (1H, quint); MS (ES+) 264.

Step 3: (R)-methyl 2-((R)-3,3-difluorocyclopentylamino)butanoate

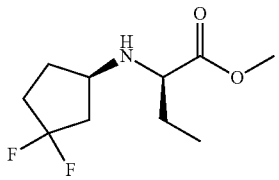

(R)-tert-butyl 2-((R)-3,3-difluorocyclopentyl amino)butanoate (1.0 g, 3.798 mmol) was dissolved in methanol (70 mL) and cooled down to 0° C. The resultant mixture was saturated with HCl gas, then stirred at room temperature for 3 hours. The reaction mixture was warmed to 40° C. for 90 minutes then concentrated under reduced pressure. The residue was partitioned between DCM and an aqueous solution of NaHCO₃. The aqueous phase was extracted with DCM three times, dried over magnesium sulfate and concentrated under reduced pressure to afford the desired product as colourless oil (645 mg, 78% yield).

¹H NMR (CDCl₃, 400 MHz): δ 0.95 (3H, t), 1.57-1.74 (3H, m), 1.83-2.09 (3H, m), 2.19-2.40 (2H, m), 3.15 (1H, t), 3.21 (1H, quint).

MS (ES+) 222.

Step 4: (R)-methyl 2-((2-chloro-5-nitropyrimidin-4-yl)((R)-3,3-difluorocyclopentyl)amino)butanoate

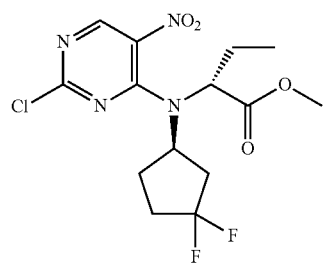 [SMILES: CC[C@H](C(=O)OC)N(c1nc(Cl)ncc1[N+](=O)[O-])[C@@H]1CCC(F)(F)C1]

2,4-Dichloro-5-nitropyrimidine (603.3 mg, 3.110 mmol) was added to a mixture of (R)-methyl 2-((R)-3,3-difluorocyclopentylamino) butanoate (688 mg, 3.110 mmol) and sodium bicarbonate (1.045 g, 12.44 mmol) in dichloroethane (5 mL) and petroleum ether (12 mL) in a sealed tube. The reaction mixture was heated at 60° C. for 4 days. The reaction mixture was diluted with dichloroethane and washed with an aqueous solution of sodium bicarbonate and brine, dried over magnesium sulfate and concentrated in vacuo. The residue was purified by flash column chromatography to afford the desired product as yellow solid (698 mg, 59% yield).

¹H NMR (CDCl₃, 400 MHz): δ 1.05 (3H, t), 1.98-2.04 (3H, m), 2.26-2.66 (5H, m), 3.71-3.76 (1H, m), 3.80 (3H, s), 3.90 (1H, quint), 8.76 (1H, s).

MS (ES+) 379.

Step 5: (R)-2-chloro-8-((R)-3,3-difluorocyclopentyl)-7-ethyl-7,8-dihydropteridin-6(5H)-one

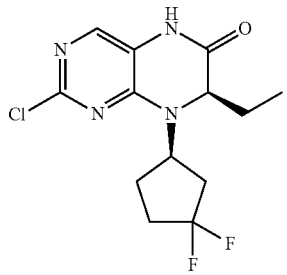 [SMILES: CC[C@@H]1C(=O)Nc2cnc(Cl)nc2N1[C@@H]1CCC(F)(F)C1]

A mixture of (R)-methyl 2-((2-chloro-5-nitropyrimidin-4-yl)((R)-3,3-difluorocyclopentyl)amino)butanoate (677 mg, 1.787 mmol) and iron powder (179.7 mg, 3.217 mmol) in glacial acetic acid (8 mL) was heated to 70° C. for 1 hours. The reaction mixture was filtered hot and the cake was further washed with acetic acid. The mother liquors were concentrated in vacuo. The residue was taken up in a 15% solution of methanol in dichloromethane and filtered through a path of silica gel rinsing with more methanol-dichloromethane solution. The mother liquors were concentrated in vacuo. The residue was triturated with ethanol and the solid was filtered to afford the desired compound as white solid (348 mg, 61% yield).

$^1$H NMR (DMSO-d6, 400 MHz) δ 0.76 (3H, t), 1.66-1.86 (2H, m), 2.03-2.24 (3H, m), 2.33-2.50 (2H, m), 2.67-2.82 (1H, m), 4.22-4.31 (2H, m), 7.61 (1H, s), 10.89 (1H, s).

MS (ES+) 317, (ES−) 315.

Step 6: (R)-7-chloro-5-((R)-3,3-difluorocyclopentyl)-4-ethyl-4,5-dihydro-[1,2,4]triazolo[4,3-f]pteridine

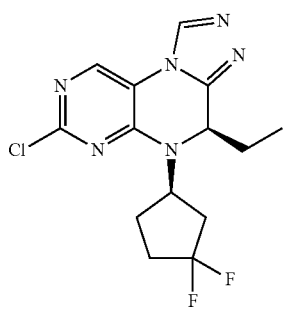 [SMILES: CC[C@@H]1C(=N)N(C=N)c2cnc(Cl)nc2N1[C@@H]1CCC(F)(F)C1]

Potassium tert-butoxide (1M in THF, 697.7 μL, 0.6977 mmol) was added at −20° C. to a solution of (R)-2-chloro-8-((R)-3,3-difluorocyclopentyl)-7-ethyl-7,8-dihydropteridin-6(5H)-one (170 mg, 0.5367 mmol) in THF (3 mL). The reaction mixture was warmed up to 0° C. for 25 minutes after complete addition. The reaction mixture was cooled down at −40° C. and diethylchlorophosphate (120.4 mg, 100.8 μL, 0.6977 mmol) was added. After complete addition, the reaction mixture was warmed up to room temperature for 45 minutes. The resulting mixture was added dropwise to 1 M hydrazine in THF (8.050 ml, 8.050 mmol) and the reaction mixture was stirred at room temperature for 18 hours. The reaction mixture was concentrated in vacuo, partitioned between DCM and an aqueous solution saturated in NaHCO$_3$. The organic phase was dried (MgSO$_4$) and concentrated in vacuo to afford a pale coloured oil (200 mg). The crude oil was dissolved in trimethylorthoformate (2.847 g, 2.935 mL, 26.83 mmol) and heated to 110° C. for 1 hour. The reaction mixture was concentrated in vacuo and purified on silica gel by flash column chromatography to afford the compound as colourless solid (0.143 gr, 78% yield).

$^1$H NMR (CDCl$_3$, 400 MHz): δ 0.85 (3H, t), 1.83-1.95 (1H, m), 2.04-2.39 (4H, m), 2.48-2.83 (3H, m), 4.43 (1H, quint), 5.19 (1H, dd), 8.33 (1H, s), 8.68 (1H, s).

MS (ES+) 341.

Step 7: 4-((R)-5-((R)-3,3-difluorocyclopentyl)-4-ethyl-4,5-dihydro-[1,2,4]triazolo[4,3-f]pteridin-7-ylamino)-N-ethyl-3-methoxybenzamide

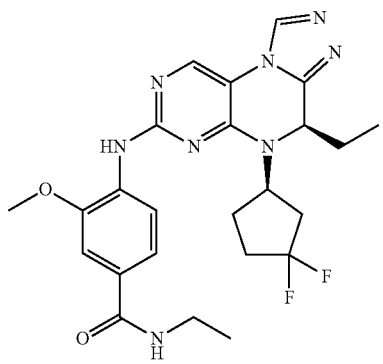 [SMILES: CCNC(=O)c1ccc(Nc2ncc3c(n2)N([C@@H]2CCC(F)(F)C2)[C@H](CC)C(=N)N3C=N)c(OC)c1]

Concentrated hydrochloric acid (36 □l) was added to a mixture of (R)-7-chloro-5-((R)-3,3-difluorocyclopentyl)-4-ethyl-4,5-dihydro-[1,2,4]triazolo[4,3-f]pteridine (70 mg, 0.21 mmol) and 4-amino-N-ethyl-3-methoxybenzamide (59.84 mg, 0.31 mmol) in ethanol (0.9 mL) and water (3.6 mL). The reaction mixture was heated to 95° C. and stirred for 18 hours. The reaction mixture was concentrated in vacuo. The residue was taken up with ethyl acetate, washed with an aqueous saturated solution of sodium bicarbonate and brine. The organic layer was dried over magnesium sulfate and concentrated in vacuo. The residue was purified on silica gel by flash column chromatography to afford the desired compound as a white solid (82 mg, 80% yield).

The compound was analyzed as a mesylate salt.

$^1$H NMR (DMSO-d6, 400 MHz) δ 0.71 (3H, t), 1.11 (3H, t), 1.79-2.34 (6H, m), 2.35 (3H, s), 2.40-2.50 (1H, m), 2.64-2.82 (1H, m), 3.27-3.34 (2H, m), 3.91 (3H, s), 4.52 (1H, quin), 5.35 (1H, t), 7.51 (1H, d), 7.56 (1H, s), 7.96 (1H, d), 8.44 (1H, t), 8.61 (1H, s), 8.89 (1H, br s), 9.30 (1H, s).

MS (ES+) 499, (ES−) 497.

Example 7

N-cyclopropyl-4-((R)-5-((R)-3,3-difluorocyclopentyl)-4-ethyl-4,5-dihydro-[1,2,4]triazolo[4,3-f]pteridin-7-ylamino)-3-methoxybenzamide

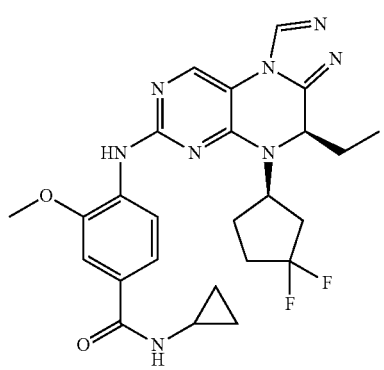 [SMILES: CC[C@@H]1C(=N)N(C=N)c2cnc(Nc3ccc(C(=O)NC4CC4)cc3OC)nc2N1[C@@H]1CCC(F)(F)C1]

This compound was analyzed a mesylate salt.

$^1$H NMR (DMSO-d6, 400 MHz) δ 0.55-0.60 (2H, m), 0.65-0.75 (5H, m), 1.76-2.30 (6H, m), 2.33 (3H, s), 2.44-2.51 (1H, m), 2.65-2.80 (1H, m), 2.80-2.90 (1H, m), 3.90 (3H, s), 4.52 (1H, quin), 5.34 (1H, q), 7.48 (1H, d), 7.50 (1H, s), 7.98 (1H, d), 8.40 (1H, d), 8.61 (1H, s), 8.77 (1H, br s), 9.30 (1H, s).

MS (ES+) 511, (ES−) 509.

Example 8

4-((R)-8-((R)-3,3-difluorocyclopentyl)-7-ethyl-5-methyl-6-oxo-5,6,7,8-tetrahydropteridin-2-ylamino)-N-ethyl-3-methoxybenzamide

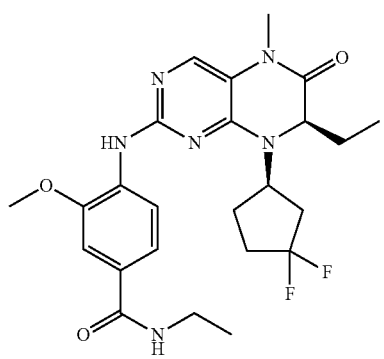 [SMILES: CCNC(=O)c1ccc(Nc2ncc3c(n2)N([C@@H]2CCC(F)(F)C2)[C@H](CC)C(=O)N3C)c(OC)c1]

Step 1: (R)-2-chloro-8-((R)-3,3-difluorocyclopentyl)-7-ethyl-5-methyl-7,8-dihydropteridin-6(5H)-one

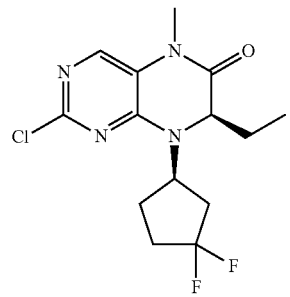 [SMILES: CC[C@@H]1C(=O)N(C)c2cnc(Cl)nc2N1[C@@H]1CCC(F)(F)C1]

60% sodium hydride in mineral oil (22.41 mg, 0.56 mmol) was added to a mixture of (R)-2-chloro-8-((R)-3,3-difluorocyclopentyl)-7-ethyl-7,8-dihydropteridin-6(5H)-one (169 mg, 0.53 mmol) and methyl iodide (36.54 μL, 0.59 mmol) in dimethylacetamide (1.7 mL). The reaction mixture was stirred at room temperature for 1 hour. Ice was added to the reaction mixture. A solid crashed out and was filtered off, rinsing with water. The solid was dried in a pistol under vacuo at 70° C. The compound was obtained as a white solid (165 mg, 94% yield).

$^1$H NMR (DMSO-d$_6$, 400 MHz): δ 0.69-0.76 (3H, m), 1.65-1.87 (2H, m), 2.07-2.37 (3H, m), 2.38-2.82 (3H, m), 3.24 (3H, s), 4.31 (1H, m), 4.43 (1H, m), 7.92 (1H, s).

MS (ES+) 331.

Step 2: 4-((R)-8-((R)-3,3-difluorocyclopentyl)-7-ethyl-5-methyl-6-oxo-5,6,7,8-tetrahydropteridin-2-ylamino)-N-ethyl-3-methoxybenzamide (I-8)

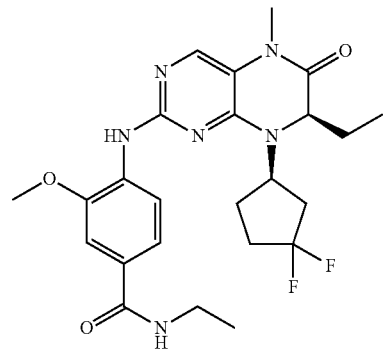 [SMILES: CCNC(=O)c1ccc(Nc2ncc3c(n2)N([C@@H]2CCC(F)(F)C2)[C@H](CC)C(=O)N3C)c(OC)c1]

Concentrated hydrochloric acid (42 μl) was added to a mixture of (R)-2-chloro-8-((R)-3,3-difluorocyclopentyl)-7-ethyl-5-methyl-7,8-dihydropteridin-6(5H)-one (80 mg, 0.24 mmol) and 4-amino-N-ethyl-3-methoxybenzamide (70.47 mg, 0.36 mmol) in ethanol (1.2 mL) and water (4.8 mL). The reaction mixture was heated to 95° C. and stirred for 18 hours. The reaction mixture was concentrated in vacuo. The residue was taken up with dichloromethane, washed with an aqueous saturated solution of sodium bicarbonate and brine. The organic layer was dried over magnesium sulfate and concentrated in vacuo. The residue was purified on silica gel by flash column chromatography to afford the desired compound as a white solid (89 mg, 75% yield).

This compound was analyzed as a mesylate salt.

$^1$H NMR (DMSO-d$_6$, 400 MHz): δ 0.75 (3H, t), 1.13 (3H, t), 1.70-2.20 (6H, m), 2.30 (3H, s), 2.40-2.50 (2H, m), 3.23 (3H, s), 3.30 (2H, quint), 3.91 (3H, s), 4.39 (1H, m), 4.50 (1H, m), 7.51 (1H, d), 7.57 (1H, s), 7.76 (1H, d), 8.87 (1H, br s), 8.47 (1H, m), 9.11 (1H, br s).

MS (ES+) 489, (ES−) 487.

Example 9

N-cyclopropyl-4-((R)-8-((R)-3,3-difluorocyclopentyl)-7-ethyl-5-methyl-6-oxo-5,6,7,8-tetrahydropteridin-2-ylamino)-3-methoxybenzamide

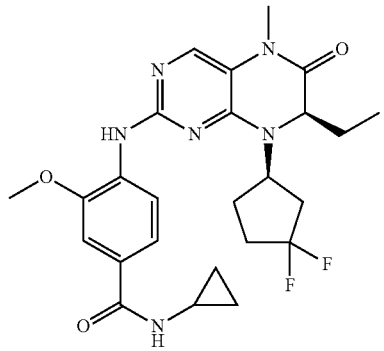 [SMILES: CC[C@@H]1C(=O)N(C)c2cnc(Nc3ccc(C(=O)NC4CC4)cc3OC)nc2N1[C@@H]1CCC(F)(F)C1]

This compound was analyzed as a mesylate salt.

$^1$H NMR (DMSO-d$_6$, 400 MHz): δ 0.55-0.59 (2H, m), 0.70-0.77 (5H, m), 1.75-2.48 (7H, m), 2.30 (3H, s), 2.50-2.70 (1H, m), 3.22 (3H, s), 3.90 (3H, d), 4.30-4.44 (1H, m), 4.53-4.57 (1H, m), 7.50 (1H, d), 7.57 (1H, s), 7.69-7.75 (2H, m), 8.47 (1H, s), 9.57 (1H, br s).

MS (ES+) 501, (ES−) 499.

Example 10

PLK Assays

The compounds of the present invention are evaluated as inhibitors of human PLK kinase using the following assays.

PLK1 Inhibition Assay:

Compounds were screened for their ability to inhibit PLK1 using a radioactive-phosphate incorporation assay. Assays were carried out in a mixture of 25 mM HEPES (pH 7.5), 10 mM MgCl$_2$, 0.1% BSA, and 2 mM DTT. Final substrate concentrations were 150 µM (350 µM for determining values of less than 1 nM) [γ-33P]ATP (115 mCi 33P ATP/mmol ATP, Amersham Pharmacia Biotech/Sigma Chemicals) and 300 µM (450 µM for determining values of <1 nM) peptide (KKKISDELMDATFADQEAK) (SEQ ID NO:1). Assays were carried out at 25° C. in the presence of 4 nM (1 nM for determining values of less than 1 nM) PLK1. An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 150 µM (350 µM for determining values of less than 1 nM))).

The reaction was stopped after 90 minutes (240 minutes for determining values of less than 1 nM) by the addition of 100 µL 0.14M phosphoric acid. A multiscreen phosphocellulose filter 96-well plate (Millipore, Cat. No. MAPHN0B50) was pretreated with 100 µL 0.2M phosphoric acid prior to the addition of 125 µL of the stopped assay mixture. The plate was washed with 200 µL 0.2M phosphoric acid for 4 times. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

In general, compounds of the invention are effective for the inhibition of PLK1. The following compounds showed Ki less than 1 nM in the radioactive incorporation assay: I-2, I-3, I-6, I-7, I-8, I-9. The following compounds showed Ki between 1 nM and 10 nM in the radioactive incorporation assay: I-1, I-4, I-5.

PLK2 Inhibition Assay:

Compounds were screened for their ability to inhibit PLK2 using a radioactive-phosphate incorporation assay. Assays were carried out in a mixture of 25 mM HEPES (pH 7.5), 10 mM MgCl$_2$, 0.1% BSA, and 2 mM DTT. Final substrate concentrations were 200 µM [γ-33P]ATP (57 mCi 33P ATP/mmol ATP, Amersham Pharmacia Biotech/Sigma Chemicals) and 300 µM peptide (KKKISDELMDATFADQEAK) (SEQ ID NO:1). Assays were carried out at 25° C. in the presence of 25 nM PLK2. An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 200 µM).

The reaction was stopped after 90 minutes by the addition of 100 µL 0.14M phosphoric acid. A multiscreen phosphocellulose filter 96-well plate (Millipore, Cat no. MAPHN0B50) was pretreated with 100 µL 0.2M phosphoric acid prior to the addition of 125 µL of the stopped assay mixture. The plate was washed with 200 µL 0.2M phosphoric acid for 4 times. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

PLK3 Inhibition Assay:

Compounds were screened for their ability to inhibit PLK3 using a radioactive-phosphate incorporation assay. Assays were carried out in a mixture of 25 mM HEPES (pH 7.5), 10 mM MgCl$_2$, and 1 mM DTT. Final substrate concentrations were 75 µM [γ-33P]ATP (60 mCi 33P ATP/mmol ATP, Amersham Pharmacia Biotech/Sigma Chemicals) and 10 µM peptide (SAM68 protein Δ332-443). Assays were carried out at 25° C. in the presence of 5 nM PLK3 (S38-A340). An assay stock buffer solution was prepared containing all of the reagents listed above, with the exception of ATP and the test compound of interest. 30 µL of the stock solution was placed in a 96-well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 75 µM).

The reaction was stopped after 60 minutes by the addition of 100 µL 0.14M phosphoric acid. A multiscreen phosphocellulose filter 96-well plate (Millipore, Cat No. MAPHN0B50) was pretreated with 100 µL 0.2 M phosphoric acid prior to the addition of 125 µL of the stopped assay mixture. The plate was washed with 200 µL 0.2 M phosphoric acid for 4 times. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

PLK4 Inhibition Assay:

Compounds were screened for their ability to inhibit PLK4 using a radioactive-phosphate incorporation assay. Assays were carried out in a mixture of 8 mM MOPS (pH 7.5), 10 mM $MgCl_2$, 0.1% BSA and 2 mM DTT. Final substrate concentrations were 15 µM [γ-33P]ATP (227 mCi 33P ATP/mmol ATP, Amersham Pharmacia Biotech/Sigma Chemicals) and 300 µM peptide (KKKMDATFADQ) (SEQ ID NO: 2).

Assays were carried out at 25° C. in the presence of 25 nM PLK4. An assay stock buffer solution was prepared containing all of the reagents listed above, with the exception of ATP and the test compound of interest. 30 µL of the stock solution was placed in a 96-well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 15 µM).

The reaction was stopped after 180 minutes by the addition of 100 µL 0.14M phosphoric acid. A multiscreen phosphocellulose filter 96-well plate (Millipore, Cat No. MAPHN0B50) was pretreated with 100 µL 0.2M phosphoric acid prior to the addition of 125 µL of the stopped assay mixture. The plate was washed with 200 µL 0.2M phosphoric acid for 4 times. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

While we have described a number of embodiments of this invention, it is apparent that our basic examples may be altered to provide other embodiments that utilize or encompass the compounds, methods, and processes of this invention. Therefore, it will be appreciated that the scope of this invention is to be defined by the appended claims.

What is claimed is:
1. A compound of formula I:

wherein

R¹ is $R^6$ is $C_{1-4}$ aliphatic or $C_{3-6}$ cycloaliphatic, and is optionally substituted with 1 or 2 halogen atoms;

X is O and $R^2$ is —$CH_3$; or X is $NR^5$ and, $R^2$ and $R^5$, together with the atoms to which they are attached, form a 1,2,4-triazole;

each of $R^3$ and $R^4$ is independently H, methyl, or ethyl; or $R^3$ and $R^4$, together with the atoms to which they are attached, form a cyclopropyl ring; and n is 0 or 1.

2. The compound of claim 1, wherein X is O and $R^2$ is —$CH_3$.

3. The compound of claim 1, wherein X is $NR^5$ and, $R^2$ and $R^5$, together with the atoms to which they are attached, form a 1,2,4-triazole.

4. The compound of claim 1, wherein $R^3$ and $R^4$ are each methyl.

5. The compound of claim 1, wherein $R^3$ is H and $R^4$ is ethyl.

6. The compound of claim 1, wherein $R^3$ and $R^4$, together with the atoms to which they are attached, form a cyclopropyl ring.

7. The compound of claim 1, wherein $R^6$ is cyclopropyl optionally substituted with 1 or 2 halogen atoms.

8. The compound of claim 1, wherein $R^6$ is cyclopentyl optionally substituted with 1 or 2 halogen atoms.

9. The compound of claim 1, wherein $R^6$ is cyclohexyl optionally substituted with 1 or 2 halogen atoms.

10. The compound of claim 1, wherein $R^6$ is $C_{1-4}$ aliphatic optionally substituted with 1 or 2 halogen atoms.

11. The compound of claim 1, wherein the compound is
N-cyclopropyl-4-(9-(3,3-difluorocyclopentyl)-5,7,7-trimethyl-6-oxo-6,7,8,9-tetrahydro-5H-pyrimido[4,5-b][1,4]diazepin-2-ylamino)-3-methoxybenzamide;
4-(9-(3,3-difluorocyclopentyl)-5,7,7-trimethyl-6-oxo-6,7,8,9-tetrahydro-5H-pyrimido[4,5-b][1,4]diazepin-2-ylamino)-N-(3-fluorocyclopentyl)-3-methoxybenzamide;
N-(3,3-difluorocyclopentyl)-4-(9-(3,3-difluorocyclopentyl)-5,7,7-trimethyl-6-oxo-6,7,8,9-tetrahydro-5H-pyrimido[4,5-b][1,4]diazepin-2-ylamino)-3-methoxybenzamide;
N-cyclopropyl-4-(9'-(3,3-difluorocyclopentyl)-5'-methyl-6'-oxo-5',6',8',9'-tetrahydrospiro[cyclopropane-1,7'-pyrimido[4,5-b][1,4]diazepine]-2'-ylamino)-3-methoxybenzamide;
N-(3,3-difluorocyclopentyl)-4-(9'-(3,3-difluorocyclopentyl)-5'-methyl-6'-oxo-5',6',8',9'-tetrahydrospiro[cyclopropane-1,7'-pyrimido[4,5-b][1,4]diazepine]-2'-ylamino)-3-methoxybenzamide;
4-((R)-5-((R)-3,3-difluorocyclopentyl)-4-ethyl-4,5-dihydro-[1,2,4]triazolo[4,3-f]pteridin-7-ylamino)-N-ethyl-3-methoxybenzamide;
N-cyclopropyl-4-((R)-5-((R)-3,3-difluorocyclopentyl)-4-ethyl-4,5-dihydro-[1,2,4]triazolo[4,3-f]pteridin-7-ylamino)-3-methoxybenzamide;
4-((R)-8-((R)-3,3-difluorocyclopentyl)-7-ethyl-5-methyl-6-oxo-5,6,7,8-tetrahydropteridin-2-ylamino)-N-ethyl-3-methoxybenzamide; or
N-cyclopropyl-4-((R)-8-((R)-3,3-difluorocyclopentyl)-7-ethyl-5-methyl-6-oxo-5,6,7,8-tetrahydropteridin-2-ylamino)-3-methoxybenzamide.

12. A pharmaceutical composition comprising a compound of claim 1 or 11, and a pharmaceutically acceptable carrier, adjuvant, or vehicle.

13. A process for preparing a compound of formula I-A:

wherein

R¹ is $R^6$ is $C_{1-4}$ aliphatic or $C_{3-6}$ cycloaliphatic, and is optionally substituted with 1 or 2 halogen atoms; and each of $R^3$ and $R^4$ is independently H, methyl, or ethyl; or $R^3$ and $R^4$, together with the atoms to which they are attached, form a cyclopropyl ring;

comprising the step of:

reacting a compound of formula 5A:

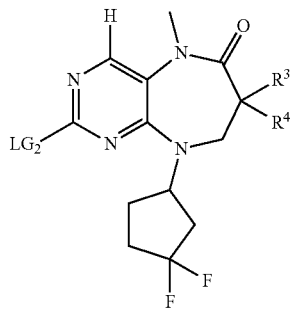

wherein $LG_2$ is a leaving group, with $H_2NR^1$ to form the compound of formula I-A.

14. The process of claim 13, further comprising the step of reacting a compound of formula 4A:

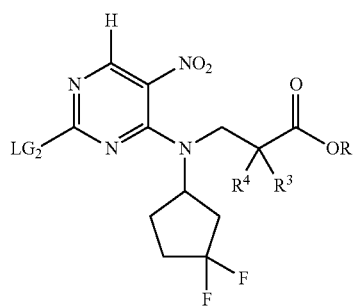

with Me-$LG_3$, wherein $LG_3$ is a leaving group capable of being displaced by a secondary amide, to form the compound of formula 5A.

15. The process of claim 14, further comprising the step of reductive cyclization of a compound of formula 3A:

wherein R is $C_{1-6}$ aliphatic or hydrogen, to form a compound of formula 4A.

16. The process of claim 14, further comprising cyclizing a compound of formula 3A-a:

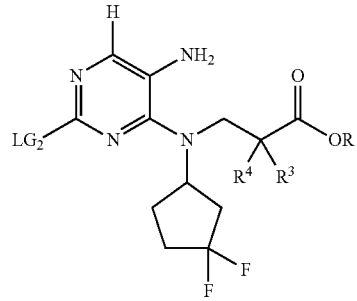

to form a compound of formula 4A.

17. The process of claim 16, further comprising the step of reacting a compound of formula 3A:

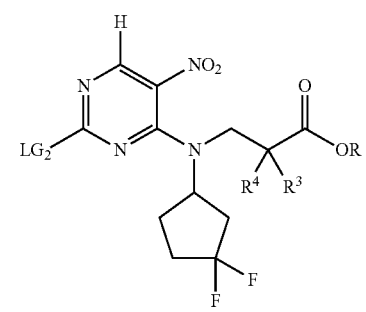

with a reducing agent to form a compound of formula 3A-a.

18. The process of claim 13 or 17, further comprising
a) reacting the compound of formula 3A-a with an alkylating agent to form a compound of formula 3A-b; and b) cyclizing the compound of formula 3A-b under suitable cyclo-condensation conditions to form a compound of formula 5A.

19. The process of claim 15, further comprising reacting a compound of formula 2a;

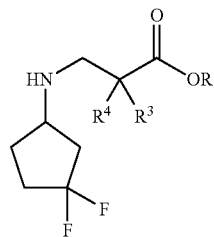

with a compound of formula 1:

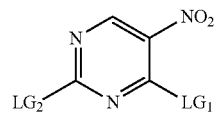

to form the compound of formula 3A.

20. The process of claim 19, further comprising reacting a compound of formula 11;

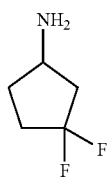

with a compound of formula 12:

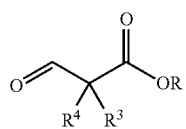

to form the compound of formula 2a.

21. The process of claim 19, further comprising
a) reacting compound of formula 11 to form hexahydro-1,3,5-triazine of formula 13; and

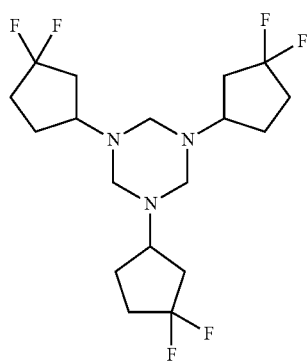

b) reacting the compound of formula 13 with a ketene silyl acetal of formula 14;

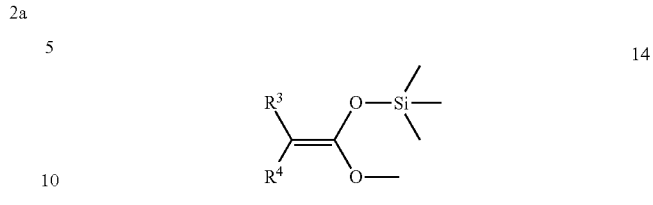

to form the compound of formula 2a.

22. A process for preparing a compound of formula I-C:

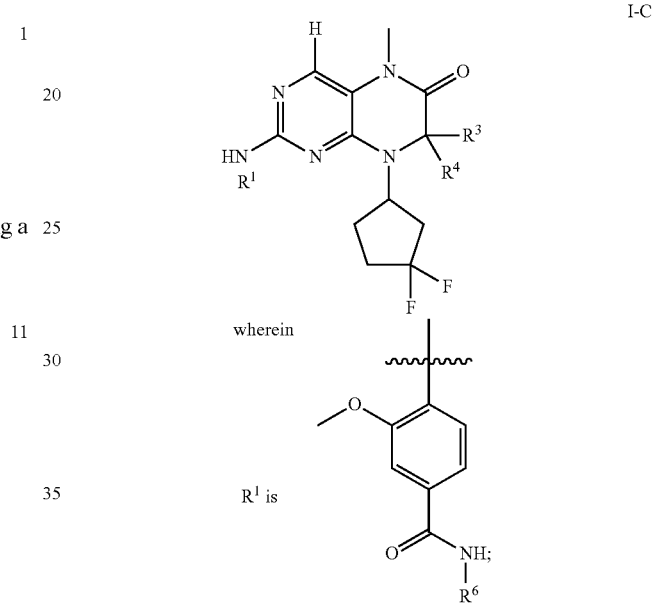

wherein $R^1$ is $R^6$ is $C_{1-4}$ aliphatic or $C_{3-6}$ cycloaliphatic, and is optionally substituted with 1 or 2 halogen atoms; and each of $R^3$ and $R^4$ is independently H, methyl, or ethyl; or $R^3$ and $R^4$, together with the atoms to which they are attached, form a cyclopropyl ring;

comprising:

reacting a compound of formula 5C:

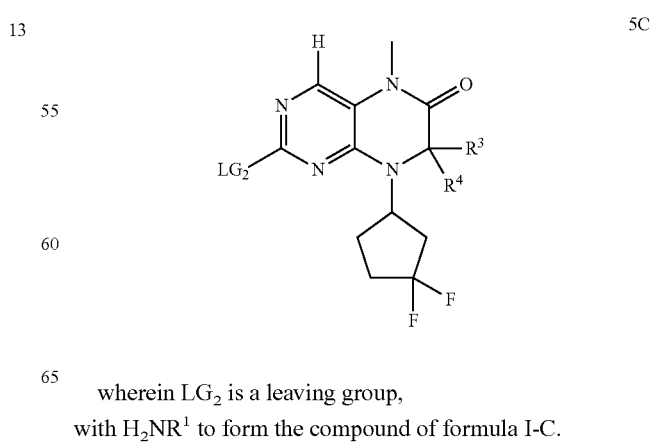

wherein $LG_2$ is a leaving group, with $H_2NR^1$ to form the compound of formula I-C.

23. The process of claim 22, further comprising the step of reacting a compound of formula 4C:

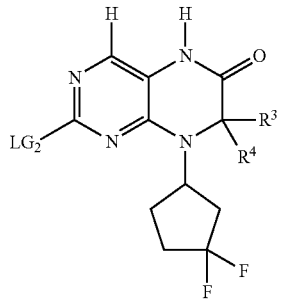

with Me-LG$_3$, wherein LG$_3$ is a leaving group capable of being displaced by a secondary amide, to form the compound of formula 5C.

24. The process of claim 23, further comprising the step of reductive cyclization of a compound of formula 3C:

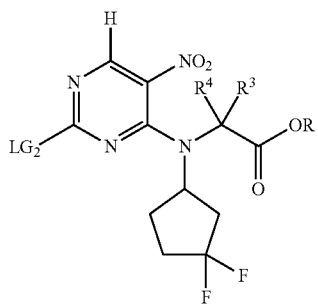

to form a compound of formula 4C.

25. The process of claim 24, further comprising cyclizing a compound of formula 3C-a:

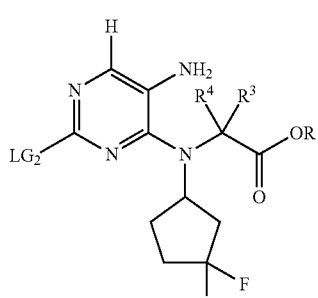

to form a compound of formula 4C.

26. The process of claim 25, further comprising the step of reacting a compound of formula 3C:

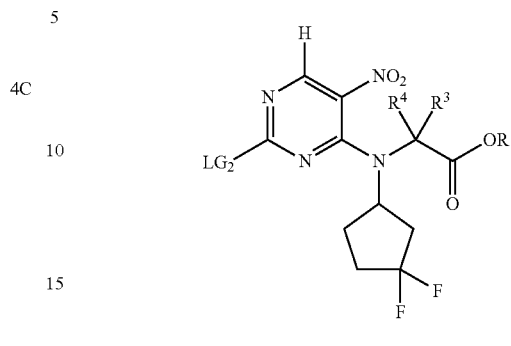

under suitable reduction conditions to form a compound of formula 3C-a.

27. The process of claim 22 or 26, further comprising
a) reacting the compound of formula 3C-a with an alkylating agent to form a compound of formula 3C-b:

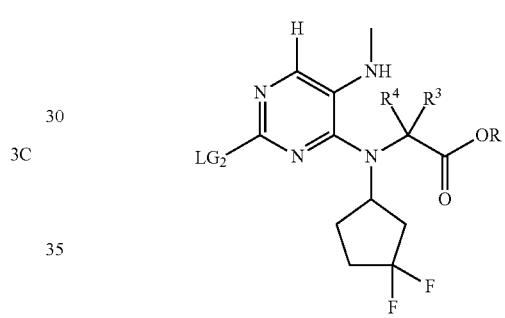

b) cyclizing the compound of formula 3C-b to form a compound of formula 5C.

28. The process of claim 24 or 26, further comprising reacting a compound of formula 2b:

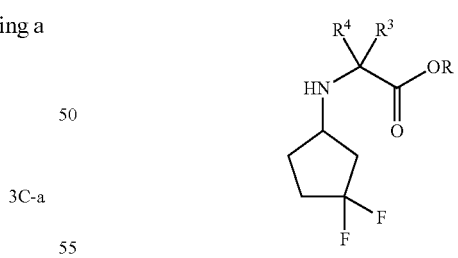

with a compound of formula 1:

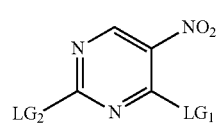

to form the compound of formula 3C.

29. The process of claim 28, further comprising reacting a compound of formula 11;

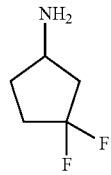

with a compound of formula 15:

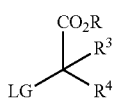

to form the compound of formula 2b.

30. A process for preparing a compound of formula I-B:

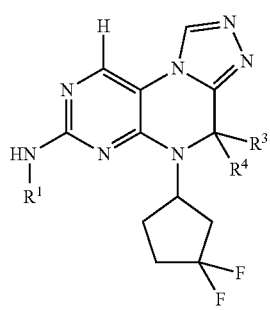

wherein

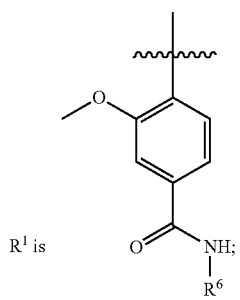

$R^1$ is $R^6$ is $C_{1-4}$ aliphatic or $C_{3-6}$ cycloaliphatic, and is optionally substituted with 1 or 2 halogen atoms; and each of $R^3$ and $R^4$ is independently H, methyl, or ethyl; or $R^3$ and $R^4$, together with the atoms to which they are attached, form a cyclopropyl ring;

comprising the step of reacting a compound of formula 10:

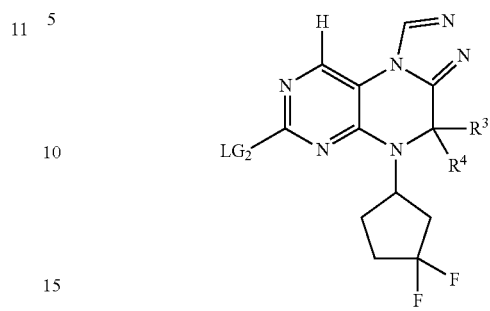

wherein $LG_2$ is a suitable leaving group, with $H_2NR^1$ under suitable conditions to form the compound of formula I-B.

31. The process of claim 30, further comprising the step of reacting a compound of formula 9:

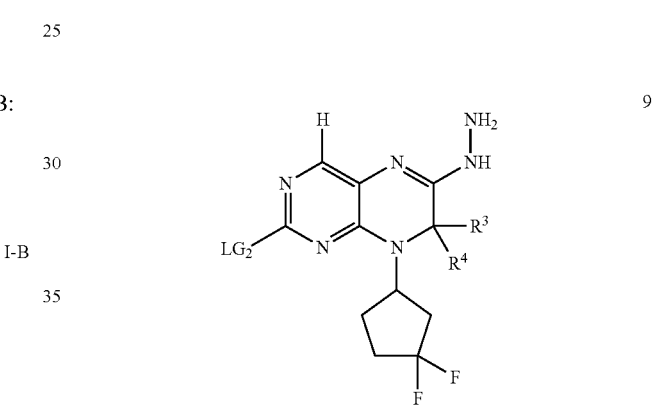

under cyclization conditions to form a compound of formula 10.

32. The process of claim 31, further comprising the step of reacting a compound of formula 8:

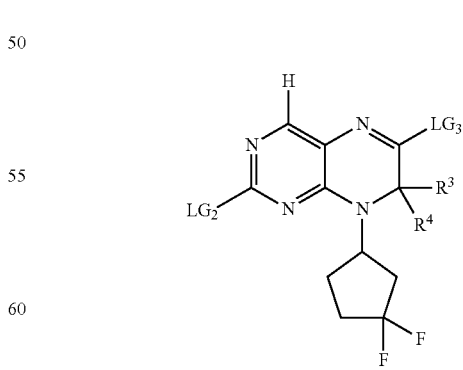

wherein $LG_3$ is a leaving group capable of being displaced by a secondary amide, with hydrazine to form the compound of formula 9.

33. The process of claim 32, further comprising reacting a compound of formula 4C:
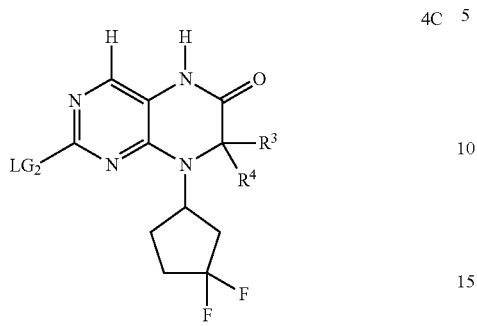
to form a compound of formula 8.
34. The process of any of claims 30-33, wherein $R^2$ and $R^5$, together with the atoms to which they are attached, form a 1,2,4-triazole.
* * * * *